United States Patent
Karube et al.

[11] Patent Number: 6,113,762
[45] Date of Patent: *Sep. 5, 2000

[54] MICROBIAL ELECTRODE AND MICROBIAL SENSOR

[75] Inventors: Isao Karube, 1-3-16, Higashiarima, Miyamae-ku, Kawasaki-shi, Kanagawa; Kiyoko Yano, Tokyo; Nobuyuki Yoshida, Omiya; Takashi Morita, Tokyo, all of Japan

[73] Assignees: Isao Karube, Kawasaki; Akebono Brake Industry Co., Ltd., Tokyo; Akebono Research And Development Centre Ltd., Hanyu, all of Japan

[*] Notice: This patent issued on a continued prosecution application filed under 37 CFR 1.53(d), and is subject to the twenty year patent term provisions of 35 U.S.C. 154(a)(2).

[21] Appl. No.: 08/913,473

[22] PCT Filed: Feb. 21, 1996

[86] PCT No.: PCT/JP96/00393

§ 371 Date: Aug. 22, 1997

§ 102(e) Date: Aug. 22, 1997

[87] PCT Pub. No.: WO96/26433

PCT Pub. Date: Aug. 29, 1996

[30] Foreign Application Priority Data

Feb. 22, 1995 [JP] Japan ................................. 7-033425

[51] Int. Cl.[7] .................................................... G01N 27/26
[52] U.S. Cl. .......................................................... 204/403
[58] Field of Search ......................... 204/403; 205/777.5; 435/817

[56] References Cited

U.S. PATENT DOCUMENTS

| | | | |
|---|---|---|---|
| 4,317,833 | 3/1982 | Sullivan | 424/283 |
| 4,898,816 | 2/1990 | Turner et al. | 435/34 |
| 5,354,679 | 10/1994 | Ohashi | 435/178 |
| 5,437,999 | 8/1995 | Diebold et al. | 435/287.9 |

OTHER PUBLICATIONS

English language translation of Riedel (DE 4301087), Jul. 1994.

CAPLUS abstract of Tanaka et al. ("Thionine and ferric chelate compounds as coupled mediators in microbial fuel cells", bioelectrochem. bioenerg. (1983); 11 (4–6), 289–97), Month Unknown.

CAPLUS abstract of Akiba et al. ("Electricity production from alkalophilic organisms", biotechnol. Lett. (1987), 9(9), 611–16), Month Unknown.

Richardson et al. ("A chemically mediated amperometric biosensor for monitoring eubacterial respiration", J. Apl. Bacteriology, 1991, 70, 422–426), Month Unknown.

Sohn et al. ("Development of Assembly for Fast BOD Estimation and Its Application", Analytical Science & Technology, 7(3), Jul. 1994, 285–291).

CAPLUS abstract of Riedel et al. (DE 4301087 A1), Jul. 1994.

*Primary Examiner*—T. Tung
*Assistant Examiner*—Alex Noguerda
*Attorney, Agent, or Firm*—Knobbe, Martens, Olson, Bear, LLP

[57] ABSTRACT

The microbial electrode is constructed having a substrate(3) made of an insulating material, an electric conductor(2) which is fixed on the substrate and a membrane containing microorganism cells(1) which is fixed on the conductor. The microbial sensor(20) is constructed having the microbial electrode above described and a conductor(11) to act as a counter electrode fixed on the insulating material of the surface of the substrate of the electrode which is opposite to the surface where the membrane containing microorganism cells is fixed.

16 Claims, 22 Drawing Sheets

(a)

(b)

F I G. 2
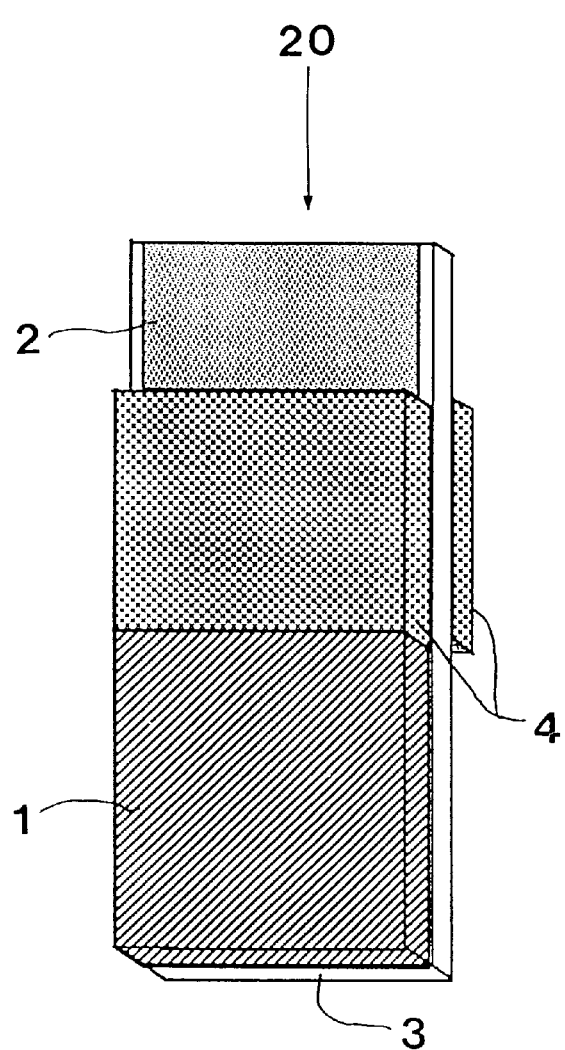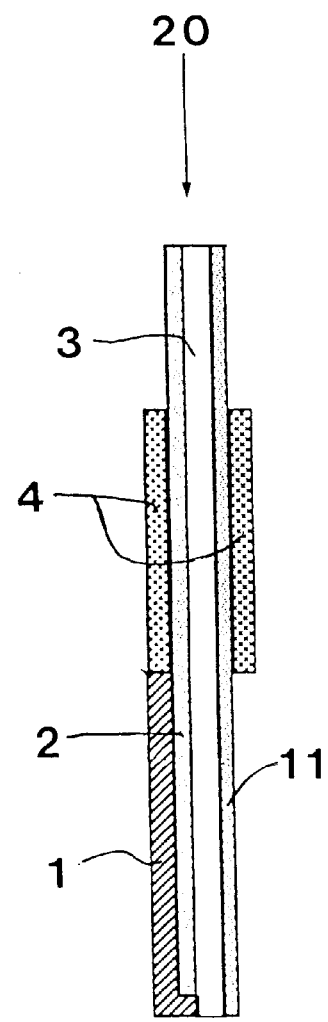
(a) (b)

(a) (b)

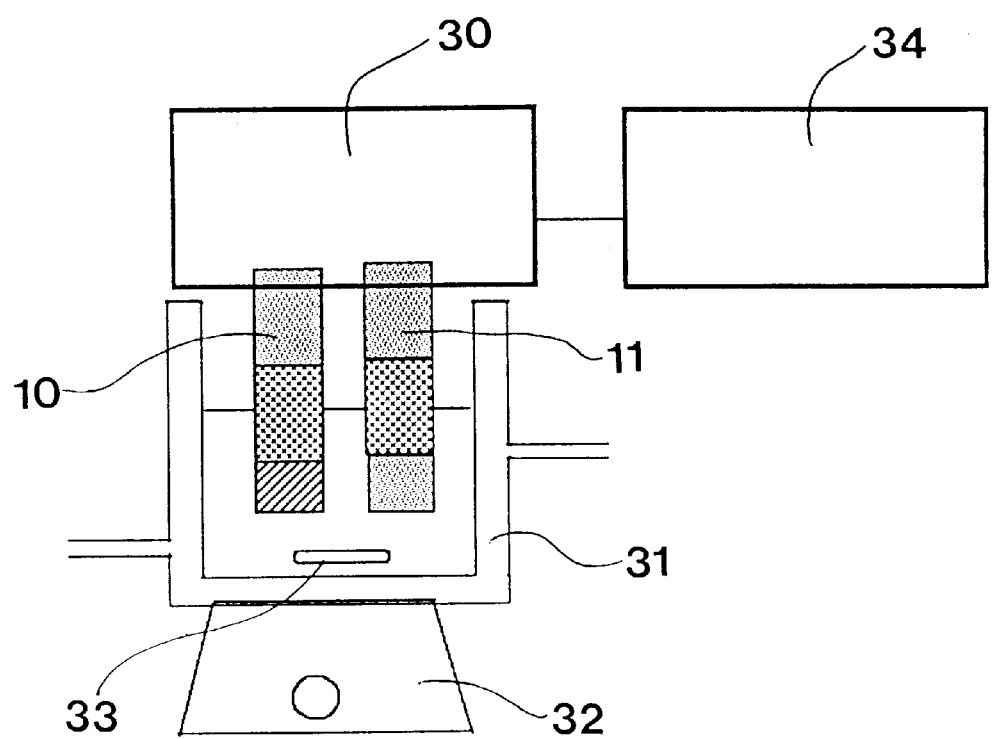
F I G. 8

F I G. 11
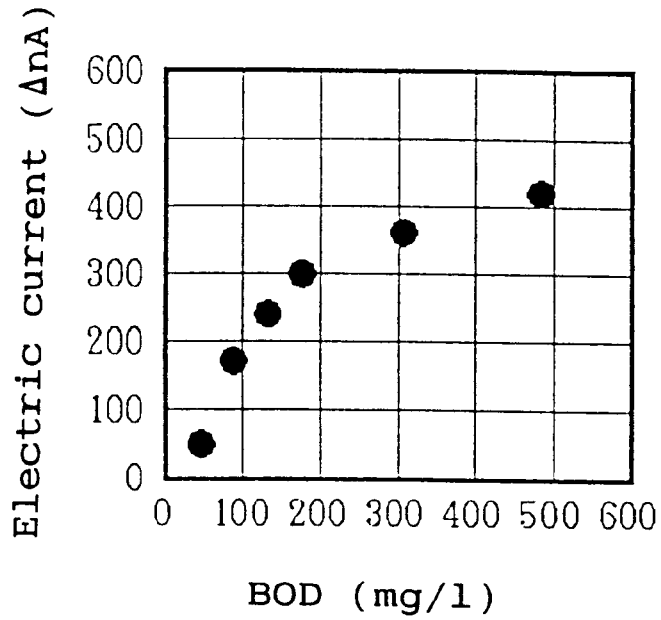
F I G. 12
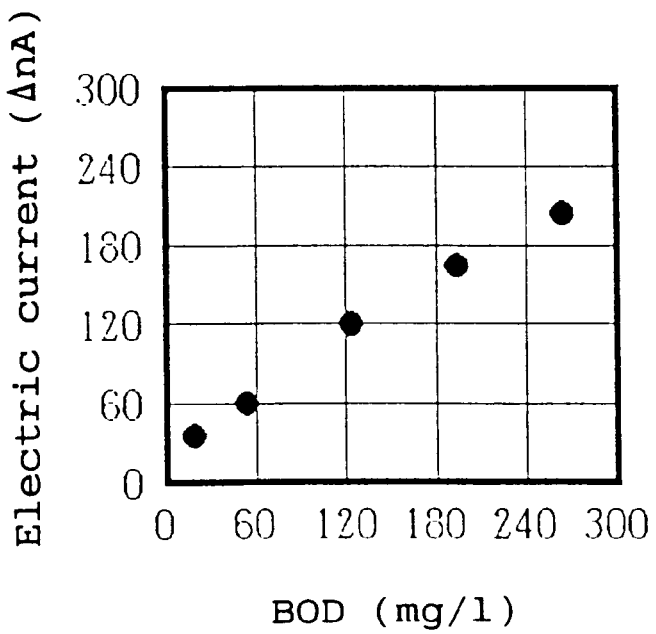

F I G. 15
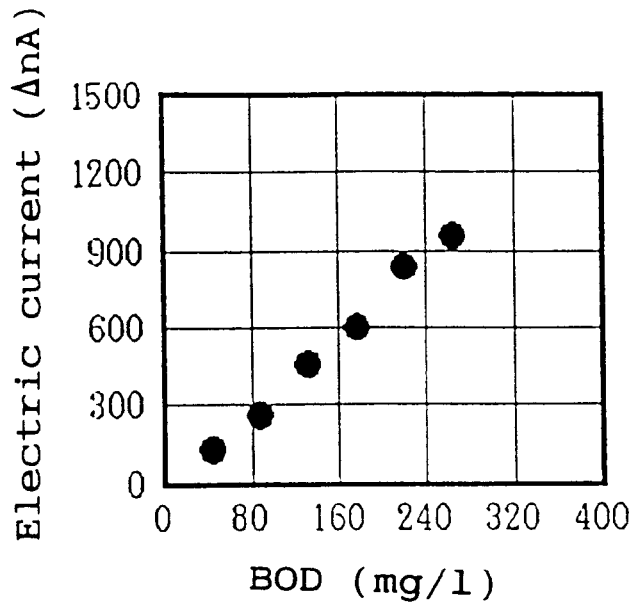
F I G. 16
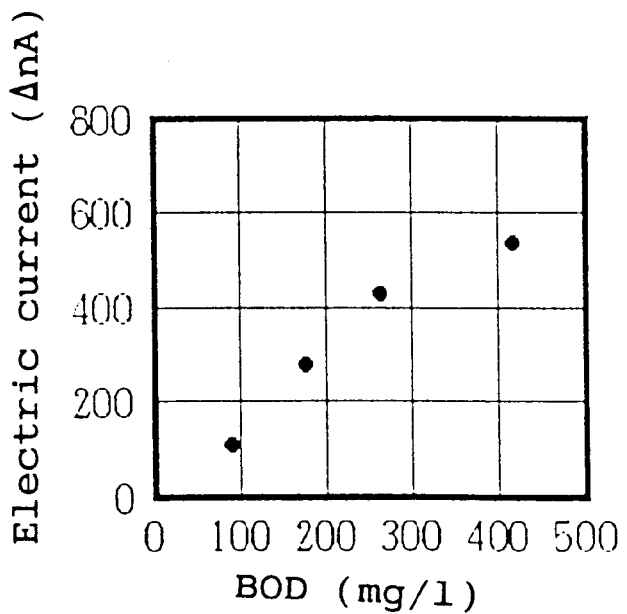

F I G. 19
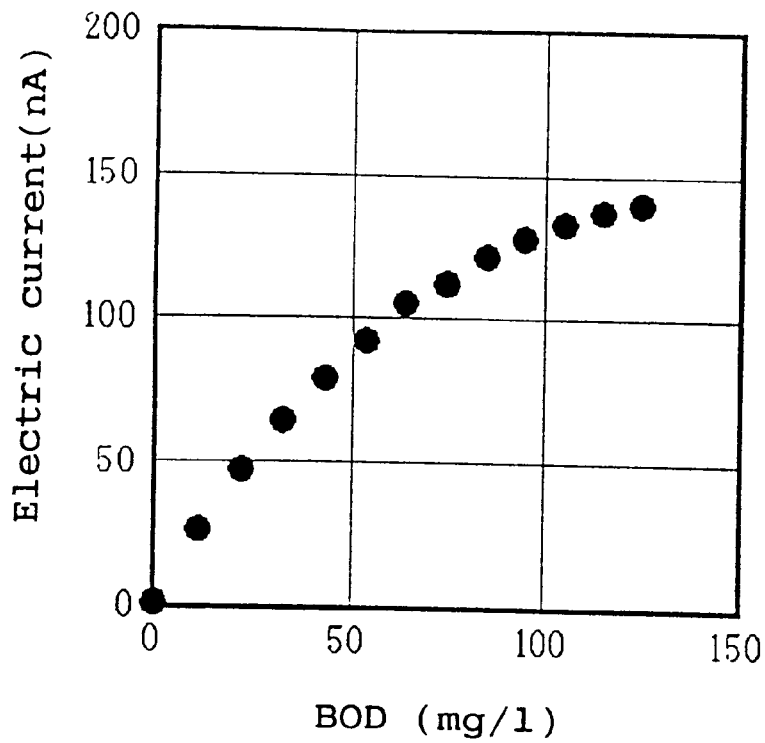
F I G. 20
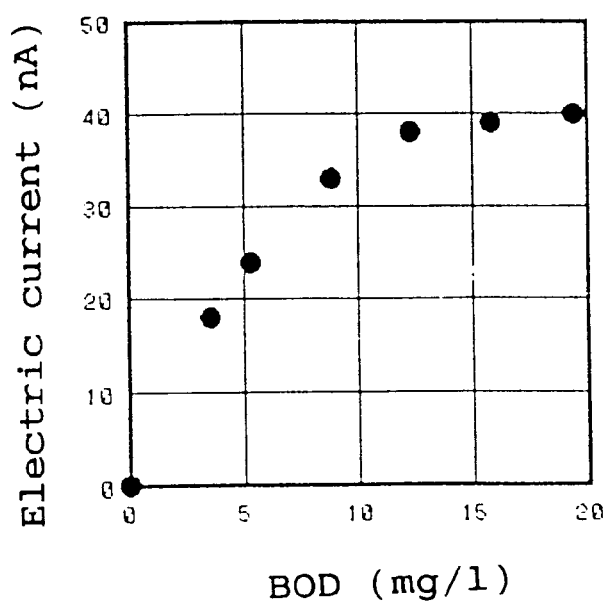

F I G. 23
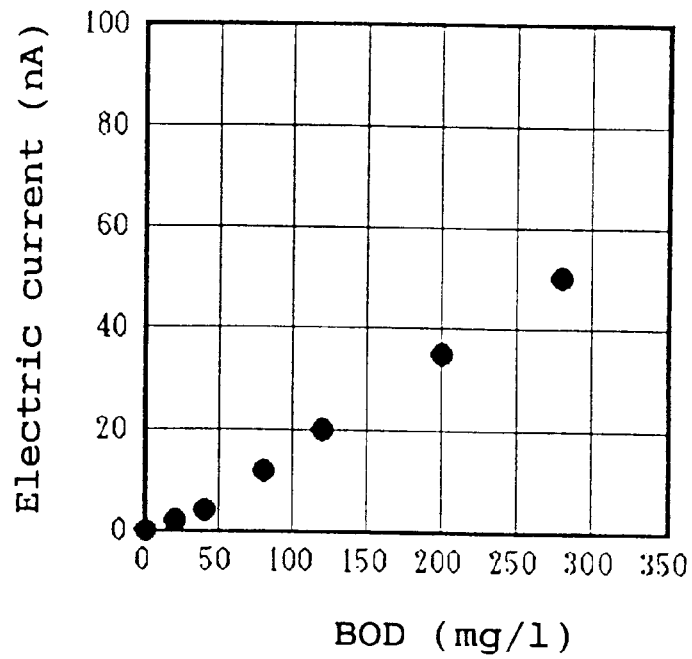
F I G. 24
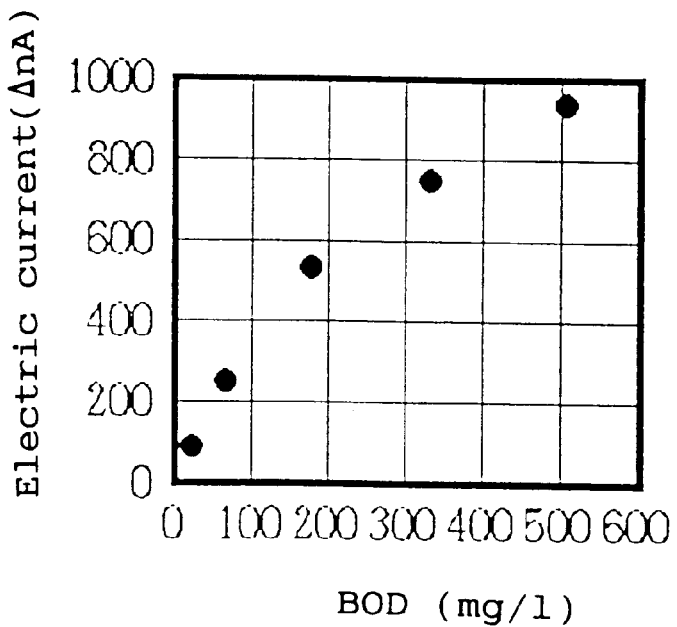

F I G. 25
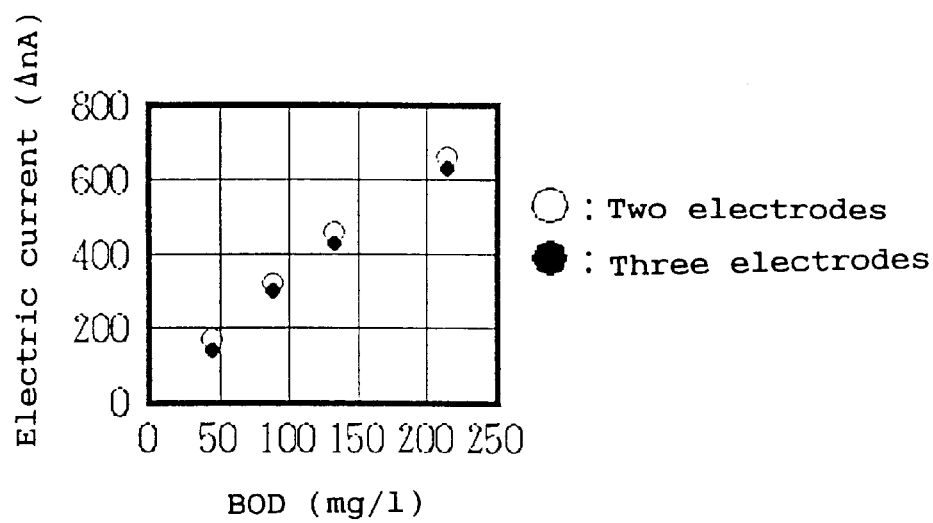
F I G. 26
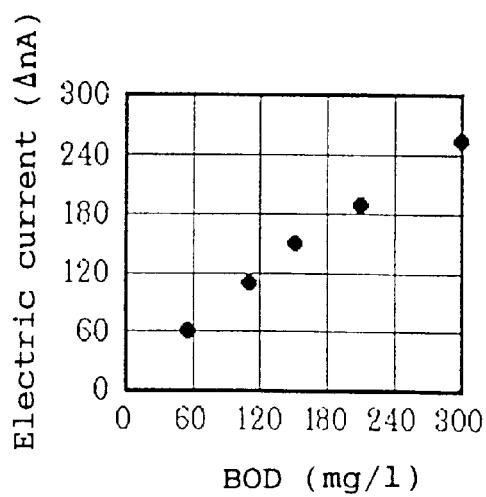

F I G. 27
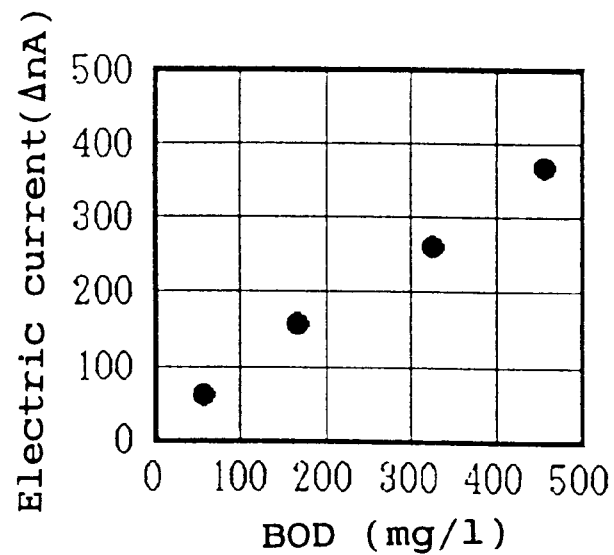
F I G. 28
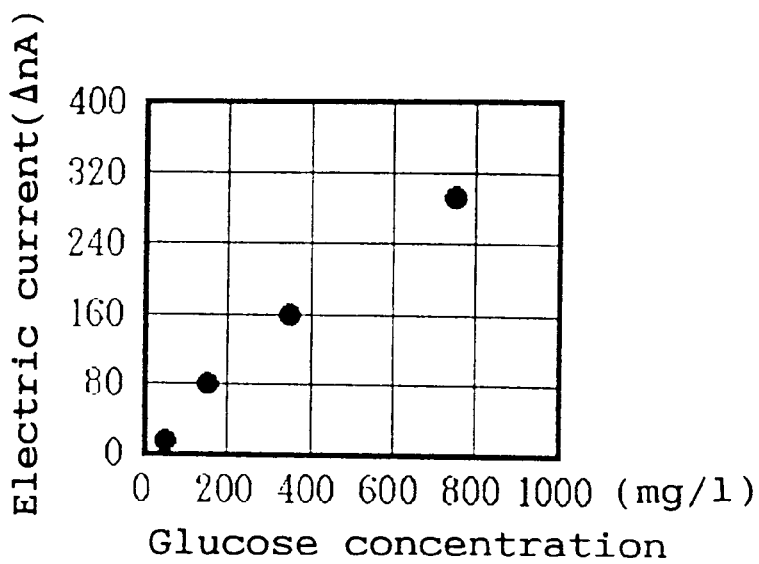

F I G. 29
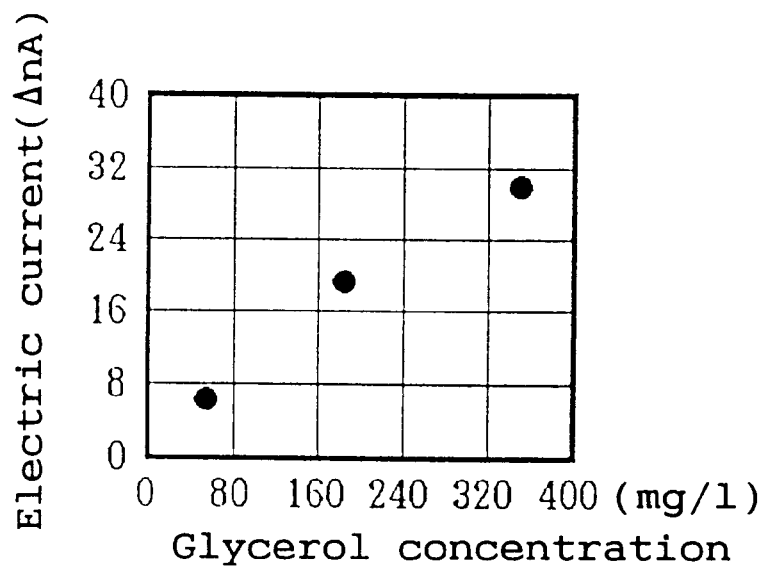
F I G. 30
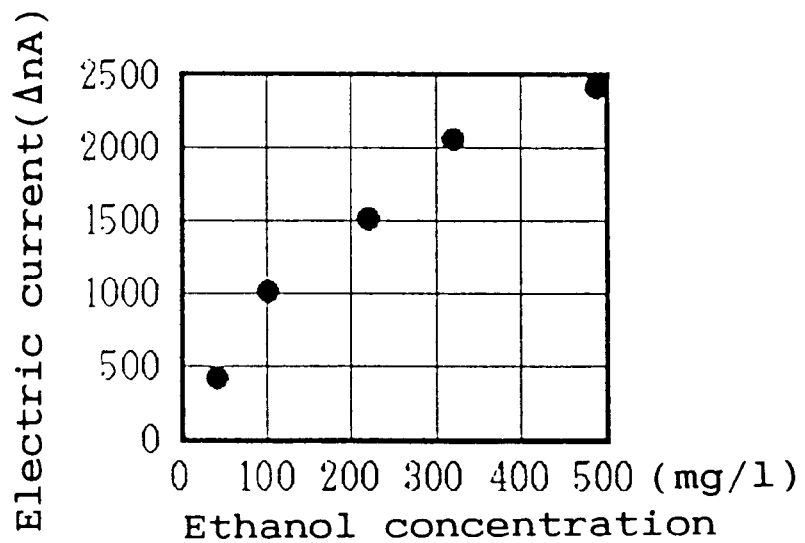

F I G. 33
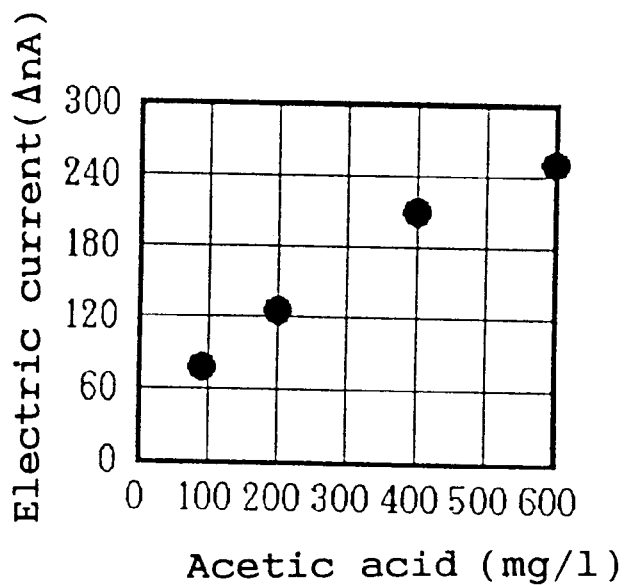
F I G. 34
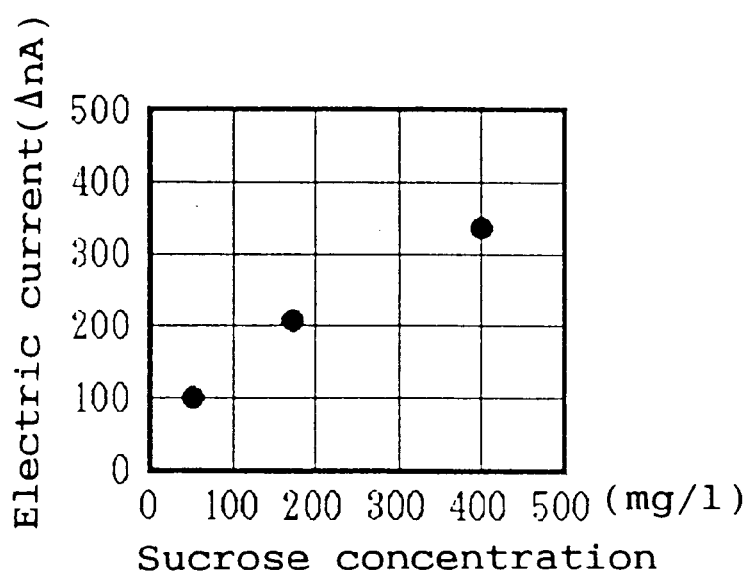

MICROBIAL ELECTRODE AND MICROBIAL SENSOR

TECHNICAL FIELD

The present invention relates to a microbial electrode and a microbial sensor, and more specifically to the microbial electrode and the microbial sensor which enable measurement of the concentration of a sample without resorting to oxygen electrodes.

BACKGROUND ART

The majority of microbial sensors which measure the concentration of a matter, measure the concentration of a matter in various solutions by utilizing a change of the microbial respiration. When microorganisms are put in a sample solution containing various matters and they metabolize those matters, their respiration is activated intensely, which will lead to reduced oxygen concentration in the environment surrounding them. Such changes in oxygen concentration are measured by oxygen electrodes, and this is the method by which a microbial sensor can measure the concentration of a substance.

For example, BOD (biochemical oxygen demand) is an important factor to be considered when the quality of water in rivers and sewage from plants must be controlled, and has been taken internationally as an indicator of the organic pollution of a water. The water pollutants derived from organic compounds are degraded through oxidation by aerobic microorganisms and consumed in the end, and in correspondence with the reduced concentration of those organic matters, dissolved oxygen is also consumed. The measurement of how much oxygen is consumed represents the pollution of a given water. In other words, BOD represents the concentration of organic compounds in terms of the oxygen consumed. A method for measuring BOD is regulated by the Japanese Industrial Standard, JIS K 0102. However, this method requires an intricate operation and it takes five days to measure BOD by this method, and hence it comes to be replaced the JIS K 0102 method by a method which allows a quick, simple and on-line measurement of BOD (JIS K 3602$^{-1990}$). As a BOD sensor for this kind of method, a BOD sensor which depends on the use of a combination of microbial film and oxygen electrodes (Japanese Laid-Open Patent Application No. 54-47699, etc.), has been provided and has been utilized for the measurement of BOD in industrial waste water or the like.

Besides BOD sensors described above, the sensor utilizing microbial activity includes a developed ethanol sensor which combines a membrane upon which are immobilized microorganisms such as *Trichosporon brassicae* which selectively consume ethanol and thus breathe vigorously in the presence of ethanol, and oxygen electrodes which measure the reduction in oxygen concentration in a solution which occurs as a result of activated respiration.

However, in the sensor described above which determines the concentration of matters in a solution by measuring the reduction in dissolved oxygen with oxygen electrodes, there is a problem that it is difficult to determine exactly the concentration of matters of a solution where dissolved oxygen remains at a low level. In addition, as the oxygen electrode must contain an electrolyte and the like within its structure, it is forced to have a certain size. Accordingly, the conventional microbial sensors which are often installed into a fermenter or the like to determine the concentration of various matters and BOD sensors described above are all large or medium in size and expensive.

DETAILED DESCRIPTION OF THE INVENTION

The present invention is made in view of the above, and it is therefore an object of the present invention to provide a microbial sensor which allows measurement even in a solution poor in dissolved oxygen, enables direct measurement of the concentration of matters in a solution without resorting to oxygen electrodes, thereby being capable of down sizing, and a microbial sensor which can be provided with reduced cost as production, and is disposable and free from reduced precision in measurement due to deteriorated microorganisms after long use.

The inventor(s) of the present invention, to solve the above mentioned problems, constructed a microbial electrode or a microbial sensor having the following structure.

That is, the present invention provides a microbial electrode which comprises: a substrate made of an insulating material; an electric conductor which is fixed on the substrate; and a membrane containing microorganism cells which is fixed on the conductor, or a microbial electrode which comprises: a substrate made of an electric conductor, and a membrane containing microorganism cells which is fixed on the substrate, and which is totally covered with an insulating coat except at least a part of the membrane containing microorganism.

Further, the present invention provides a microbial sensor characterized by comprising: the above mentioned microbial electrode and; a conductor to act as the counter electrode and fixed on the insulating material of the surface of the substrate of the electrode which is opposite to the surface where the membrane containing microorganism cells is fixed. The present invention further provides a microbial sensor characterized by comprising: the above mentioned microbial electrode; a substrate made of an insulating material arranged with facing to the membrane containing microorganism cells of the electrode; a conductor to act as the counter electrode and fixed on the surface of the substrate facing to the membrane containing microorganism of the substrate; and a sample liquid holding member having absorption property inserted and fixed between the conductor and the membrane containing microorganism.

Still further, the present invention provides a microbial sensor characterized by comprising: a substrate made of an insulating material; two conductors fixed on one surface of the substrate so as not to have any physical contact with each other; and a membrane containing microorganism which is fixed on one of the two conductors, or a microbial sensor which comprises: a first substrate; a first conductor to act as an electrode and fixed on the surface of the first substrate; a second substrate with an opening and made of an insulating material, which, facing through the opening on the first conductor, covers the first conductor; a second conductor to act as the counter electrode fixed on the surface of the second substrate; a membrane containing microorganism which is fixed on the first conductor and inside of the opening of the second substrate; and a frame which having an opening forming a sample liquid accumulation portion and facing through the opening on the membrane containing microorganism and the second conductor, covers the second conductor.

Furthermore, the present invention provides a sample liquid collecting unit characterized by comprising: a sample liquid sucking inlet; a liquid accumulation portion for storing sample liquid sucked through the sample liquid sucking inlet; and an aspiration pump for generating an aspirating power, which incorporates above mentioned microbial sensor in the sample liquid accumulation portion.

The present invention will be described in detail below.
<1> Microbial electrode of the present invention The microbial electrode of the present invention is comprised of a substrate made of an insulating material, an electric conductor fixed on the substrate and a membrane containing microorganism cells which is fixed on the conductor.

The microbial electrode of the present invention, when used in combination with a counter electrode or with a counter electrode and a reference electrode, may be utilized as a microbial sensor to measure the concentration of matters in various kinds of solutions.

When microorganisms are allowed to exist in a sample solution containing organic compounds, the microorganisms metabolize those organic compounds to acquire energy. During the metabolysis, transfer of electrons occurs in the electron transport system of its respiratory chain. Also, some microorganisms metabolize inorganic matters to acquire energy, and during the metabolysis transfer of electrons occurs, too.

At this time, the concentration of matters metabolized correlates to the amount of electrons that are transferred. Therefore, it is possible to determine the concentration of matters around the microorganisms by measuring the amount of transferred electrons. Since it is difficult to directly measure the transferred amount of electrons, according to the present invention, a microbial electrode having the above described structure is immersed in a sample solution in combination with a counter electrode or with a counter electrode and a reference electrode, and a certain potential difference is applied between the microbial electrode acting as the working electrode and the counter electrode or the reference electrode such that the electrons easily transfer to measure the current flowing between both the electrodes so that the concentration of matters in the sample solution can be determined. The structure of the microbial electrode of the present invention will be described below.

The microorganism to be applied to the electrode of the present invention includes any kind of microorganisms as long as they allow electrons to tranfer through the electron transport system while they metabolize organic or inorganic matters, and should not be limited to any specific microorganisms. The microorganism may include a procaryote and an eucaryote, but the procaryote is more preferred, as far as the sensitivity in the measurement of the concentration of matters in a solution is concerned, than the eucaryote because in cells of the latter the electron transfer through the electron transport system of its respiratory chain is conducted in the mitochondria which makes it difficult to readily detect the amount of electrons that transfer to the working electrode (microbial electrode) as the electric current.

When the microbial electrode of the present invention is applied for determination of the concentration of matters in a solution, it is preferable to choose appropriate microorganisms which can metabolize the matters the concentration of which is to be determined. Further, when the concentration of one matter out of various kinds of matters contained in a solution is to be measured, it may be prepared a microbial electrode with using a microorganism which can metabolize the matter whose concentration is to be determined. Thus, there are appropriate combinations between matters to be determined and microorganisms to metabolize them. For BOD determination, it may be available for the microorganism to allow electrons to transfer through the electron transport system while it metabolizes organic matters, and such microorganism may include procaryotes such as *Escherichia coli*, bacteria of belonging to the genus Bacillus, genus Acinetobacter, genus Gluconobacter, and genus Pseudomonas, and actinomycetes and eucaryotes such as yeast of belonging to the genus Trichosporon. Other recommendable combinations between matters to be determined and microorganisms to metabolize them are cited below.

*Pseudomonas aerginosa* and the like for polyethyleneglycol; *Pseudomonas cepacia, Pseudomonas fulva* and the like for phthalate esters; Acinetobacter, *Pseudomonas putida, Pseudomonas paucimobilis* and the like for polybiphenylchloride; *Pseudomonas putida* and the like for phenol; *Clostridium cochlearium* and the like for organomercury compounds; *Methylomonas methylovara, Hansenula polymorpha* and the like for methanol; *Hansenula angusta, Candida mycoderma, Gluconobacter rubiginosus* IFO3244 and the like for ethanol; *Pseudomonas aerginosa* and the like for cadmium; *Pseudomonas putida, Pseudomonas convexa* and the like for toluene; *Pseudomonas ovalis* and the like for m-xylene; *Desulfovibrio deseulfuricans, Thiobacillus thiooxidans, Thiobacillus thioparus* and the like for organosulfur; *Pseudomonas alcaligenes* and the like for dibenzothiophene; *Clostridium butyricum* and the like for formic acid; *Methylococus capsulatus, Methylosinus trichosporium* and the like for methane gas; *Arthrobacter petroleophagus, Mycobacterium petroleophilum* and the like for ethane gas; *Lactobacillus arabinosas* and the like for nicotinic acid; *Brevibacterium cacaveris* and the like for aspartic acid; *Gluconobacter suboxydans* IFO3172 and the like for glucose; *Pseudomonas fluorescens* IFO14160 and the like for glycerol; *Pseudomonas putida* IFO14164 for L-glutamic acid; *Pseudomonas pseudomallei* ATCC15682 and the like for maltose; *Bcillus subtilus* IFO13719 and the like for acetic acid; *Pseudomonas caryophylli* IFO13591 and the like for sucrose; and *Pseudomonas putida* IFO14164 and the like for S. starch. They are cited as appropriate combinations between matters to be determined and microorganisms to metabolize them just for illustration, and the present invention is not limited to those combinations.

Such microorganisms as described above are incorporated into the microbial electrode of the present invention, and the microorganism, to be used as an electrode, is contained in a membrane. This microorganism containing membrane, for making the microorganism cells present on or near the surface of the conductor as the electrode fixed on the substrate made of an insulating material, and may take any form as long as it is thin. Microorganism cells, for example, may be included into a gel matrix of an alginate gel membrane, a carrageenan gel membrane, an agarose gel membrane, a curdlan gel membrane, a chitosan gel membrane, or the like, or into a photo-setting resin membrane such as a photo-crosslinkable polyvinyl alcohol membrane, or into a three-dimensional crosslinked structure of a polyacrylamide membrane or the like.

Further, microorganism cells may be immobilized with a polymer membrane. Furthermore, as another modification, microorganisms may be immobilized with glutaraldehyde or the like in membranous form on the surface of the substrate which is an element of the microbial electrode so that electric connection can be readily made with the conductor as the electrode. As a further modification, microorganisms can be immobilized using an appropriate combination of above methods according to given purposes. Microorganisms in the membrane are preferably alive.

The substrate to form an element of the microbial electrode of the present invention supports the conductor acting as an electrode and the membrane containing microorganism cells, and is insulating because it must prevent electric current from flowing between the above conductor and the counter electrode when the assembly is used a microbial sensor. In other words, the substrate to form an element of the microbial electrode of the present invention may be made of any materials and is not limited to any specific ones, as long as it is sufficiently strong to firmly support the conductor and the membrane containing microorganism cells and has an insulating property in a solution. It may be made of, for example, plastics such as polyester, glass, and paper whose surface has been so treated as to prevent the invasion of a sample solution. According to the present invention, the substrate is preferably made of a porous material because such material prevents the membrane containing microorganism cells from being peeled off.

The conductor acting as an electrode to form another element of the microbial electrode of the present invention is fixed on the substrate in such a manner that it is electrically connected to the membrane containing microorganism cells, and receives electrons which are generated in association with the metabolic activity of the microorganisms exposed to matters to be determined in a sample solution. The conductor may be made of any material as long as it is stable, highly electroconductive, and substantially innocuous to the microorganisms, and may include metals such as platinum, gold and silver, and carbonaceous materials such as graphite and carbon. It may take any form, but is preferably shaped like a bar, a cylinder or a sheet. It is preferably so prepared as to make the contact area with the membrane containing microorganism cells as large as possible.

For example, the conductor may be made into a conductive layer and be fixed on one surface of the insulating substrate, thereby being possible for the conductor to have as large a contact area with the membrane containing microorganism cells as possible. One example of the microbial electrode includes one where a metal layer is formed by deposition on one surface of the substrate, and the membrane containing microorganism cells is fixed on the metal layer.

Further, the conductor of the microbial electrode of the present invention is installed in such a manner that it may not come into contact with a sample solution directly. This is to prevent electric current from flowing between the conductor in question and the counter electrode when the microbial electrode of the present invention is immersed into the sample solution. If the structure of the microbial electrode happens to allow part of its electric conductor to come into contact with the sample solution, and electric current to leak therethrough, that part must be electrically insulated with some insulating material. For example, in the case where the electric conductor fixed on the substrate of the microbial electrode is exposed from the microorganism cell, to thereby have a part which comes into contact with the sample solution, tinsulatedhat part must be electrically insulated with insulating material such as an epoxy resin.

Here, it is possible to make the substrate and conductor of the microbial electrode of the present invention from the same material as appropriate according to given purposes.

In other words, according to another aspect of the present invention, the microbial electrode has a structure comprising a substrate made of a electroconductive material, and a membrane containing microorganism cells which is firmly fixed on the substrate, and has the whole covered with an insulating coat except at least a part of the membrane containing microorganism cell.

This type of microbial electrode obviates the necessity of fixing a conductor to a substrate as in the above described microbial electrode, because it incorporates a substrate made of a conductive material. Thus, with this electrode, the substrate itself acts as an electrode. However, with this microbial electrode, it is necessary to electrically insulate the surface on which the membrane containing microorganism cells is not fixed, that is, all the part of the substrate which may possibly come into contact with a sample solution directly, so that electric current can be effectively prevented from flowing between the conductor and the counter electrode when the microbial electrode is immersed into the sample solution.

In the actual use, which one of the two aspects of microbial electrodes of the present invention should be selected is appropriately determined in consideration of the kinds of the conductor or the like.

A microbial sensor incorporating above described microbial electrode of the present invention comprises, in addition to the microbial electrode acting as the working electrode, a counter electrode, and further a reference electrode as needed. The counter electrode may be made of platinum, silver, gold, carbon or the like. It sometimes happens that, when the microbial sensor is immersed into a measurement sample solution and the potential difference is applied between the working electrode (microbial electrode) and the counter electrode, the concentration of the reaction materials on the surface of the electrode decreases, and the concentration of the products increases as the reaction of the electrode proceeds. This may lead to a shift of the potential of the electrode difference from the set potential. Therefore, it is preferred to immerse a reference electrode such as an Ag/AgCl electrode or the like into a sample solution, and to set the potential of the working electrode on the basis of the reference electrode (3-electrode method).

Furthermore, when a sample solution contains a plurality of matters to be determined, it is desirable and possible to incorporate a plurality of microbial electrodes each comprising a membrane containing microorganism corresponding to the individual matter to be determined, and the counter electrodes, and further the reference electrodes as needed, into a microbial sensor which allows the synchronous measurement of a plurality of matters contained in the same sample solution.

<2> Microbial sensor and sample liquid collecting unit of the present invention

The microbial sensor of the present invention may be produced such that, as described above, a microbial electrode, a counter electrode and a reference electrode as needed may be formed separately. However, according to the present invention, the microbial electrode and the counter electrode are integrally formed so as to form the microbial sensor in a small size or to simplify the measurement.

To obtain the microbial sensor in which the microbial electrode and the counter electrode is integrally formed as described above, the microbial sensor of the present invention has the following structure.

According to present invention, the microbial sensor is comprised of the microbial electrode of the present invention described above, and a conductor to act as the counter electrode which is fixed on the insulating material of the surface of the substrate of the electrode which is opposite to the surface on which the membrane containing microorganism cells is fixed.

Alternatively, the microbial sensor of the present invention is comprised of the above mentioned microbial electrode, a substrate made of an insulating material arranged with facing to the membrane containing microorganism cells of the electrode, a conductor to act as the counter electrode and fixed on the surface of the substrate facing to the microorganism containing membrane of the substrate, and a sample liquid holding membre having absorption property inserted and fixed between the conductor and the membrane containing microorganism cells. Since the microbial sensor with the sample liquid holding member is integrally formed of the microbial electrode and the counter electrode, and allows the holding member to hold sample liquid, the microbial sensor may be used, for example, for the measurement of the concentration of a matter contained in a small volume of a sample liquid kept at the bottom of a beaker. Further, a sample liquid may be collected with this microbial sensor itself, for example, from a big tank, and may be immediately subjected to measurement, thus is convenient.

These microbial sensors are constructed so that the conductor of the microbial electrode may not make a direct contact with a sample solution to prevent, as discussed above, electric current from flowing directly between the microbial electrode and the counter electrode. Otherwise, when the conductor of the microbial electrode structurally includes a part which may directly contact with a sample solution, that part is electrically insulated with an insulating coat made of an epoxy resin or the like so that a leak current may not flow therethrough. Such insulating coating treatment may also be applied to the conductor acting as the counter electrode so that the counter electrode may have the same contact area with a sample solution whenever it is immersed into the solution.

Furthermore, another aspect of a microbial sensor in which a microbial electrode of the present invention and a counter electrode are integrally formed, includes a microbial sensor comprising a substrate made of an insulating material, two conductors fixed on one surface of the substrate so as not to have any physical contact with each other, and a membrane containing microorganism cells which is fixed on one of two conductors described above. Of these two conductors which are so fixed on the substrate of the microbial sensor as not to physically contact with each other, one acts as the counter electrode as it is, while the other conductor, on which the membrane containing microorganism cells being fixed as in the above mentioned microbial electrode of the present invention, acts as the microbial electrode (working electrode). In other words, this microbial sensor of the present invention includes the microbial electrode and the counter electrode on the same surface of the same substrate.

Further, in this type of microbial sensor of the present invention, a spacer having a sample liquid pouring inlet and a cover are laminated on the surface of the substrate on which a membrane containing microorganism cells is formed, to thereby form a sample liquid holding portion which is surrounded with the surface of the substrate on which a conductor and a membrane containing microorganism cells are formed, the internal wall of the spacer, and the lower edge of the cover. Furthermore, in the microbial sensor of the present invention, a sample liquid holding member having absorption property is provided in the sample liquid holding portion, to thereby provide the microbial sensor which enables a sample liquid to be spontaneously injected into the sensor to measure the concentration of the matter therein. In this case, furthermore, it is preferred to install a filter onto the sample liquid pouring inlet so that the measurement is not interfered by floating matters or the like in the sample liquid which is poured through the inlet and adhere onto the electrodes. Further, the cover preferably has an air vent which faces on a part of the sample liquid holding portion so that the sample liquid may smoothly enter thereto.

Further, when this microbial sensor is applied for the simultaneous measurement of the concentration of various matters to be measured and contained in a sample solution, the number of conductors to be formed so as not to contact with each other on the substrate of the microbial sensor should be the number of matters to be measured plus one (one represents the number of the conductor to act as a counter electrode), and to each conductor to act as an working electrode (excluding the counter electrode) is fixed a membrane containing a microorganism appropriate for the measurement of a matter to be measured.

In this case, according to the microbial sensor of the present invention, the conductor to act as the microbial electrode is mounted so that it may not have a direct contact with a sample solution, when the microbial sensor is immersed into the sample solution, in order to prevent electric current from directly flowing between the conductor to act as the microbial electrode and the conductor to act as the counter electrode. Further, when the conductor of the microbial electrode structurally includes a part which may directly contact with a sample solution, that part is electrically insulated with an insulating coat made of an epoxy resin or the like. Similar treatment such as the insulating coating may also be applied to the conductor to act as the counter electrode so that the counter electrode may have the same contact area with a sample solution whenever it is immersed into the solution.

Furthermore, on the surface of the substrate of the above mentioned microbial sensor on which a conductor (counter electrode) and a microbial electrode (working electrode) are formed, a reference electrode is formed so as not to contact with the working electrode and a counter electrode with each other, thereby being capable of providing a microbial sensor incorporating three electrodes (working electrode, counter electrode and reference electrode) in one unit.

Such conductors to be used for the respective microbial sensors of the present invention may be made of the same materials as that of the microbial electrodes of the present invention. Also the insulating substrate onto which the conductors are fixed, may be made of the same material as that of the microbial electrode of the present invention. According to one aspect of a microbial sensor of the present invention, a sample liquid holding member having absorption property is inserted for fixing between a conductor to act as a counter electrode and a membrane containing microorganism cells. According to another aspect of a microbial sensor of the present invention, a sample liquid holding portion in which a sample liquid holding member having absorption property is provided, is installed as a part of the microbial sensor in the sensor. The sample liquid holding member may be made of any materials, as long as the material can absorb a give amount of sample liquid and hold it, and is not limited to any specific materials. The material includes, for example, sponge, nylon mesh and the like. Further, the spacer and the cover which are used in a microbial sensor having a sample liquid holding portion within its structure as a part of the microbial sensor may be made of the same materials as are used for the insulating substrate of the microbial electrode of the present invention.

When such microbial sensor is used for the measurement of the concentration of matters contained in a sample solution, the microbial sensor is immersed into the measurement sample solution, a certain potential difference is applied between the working electrode (microbial electrode)

and the counter electrode so that the electrons may transfer easily between them, and an electric current flowing between both the electrodes is measured, thereby being capable of measuring the concentration of matters in the sample solution. Also in this case, as described above, it is possible to immerse a reference electrode such as an Ag/AgCl electrode or the like into the sample solution together with the microbial sensor, and to set the potential of the working electrode on the basis of the reference electrode.

Furthermore, according to the present invention, another aspect of a microbial sensor in which a microbial electrode and a counter electrode are integrally formed into one unit, is comprised of a first substrate, a first conductor to act as an electrode and fixed on the surface of the first substrate, a second substrate with an opening and made of an insulating material, which, facing through the opening on the first conductor, covers the first conductor, a second conductor to act as the counter electrode fixed on the surface of the second substrate, a membrane containing microorganism cells which is fixed on the first conductor and inside of the opening of the second substrate, and a frame which having an opening forming a sample liquid accumulation portion and facing through the opening on the microorganism containing membrane and the second conductor, covers the second conductor.

The membrane containing microorganism cells which is incorporated into the microbial sensor of the present invention may be made of the same materials as are used for the membrane containing microorganism cells of the microbial electrode of the present invention. Further, the first conductor to act as an electrode and the second conductor to act as a counter electrode of the microbial sensor of the present invention may be made of the same materials as those for the conductors of the microbial electrode of the present invention. Furthermore, the first substrate, the second substrate, and the frame of the microbial sensor may be made of the same insulating materials as are used for the substrate of the microbial electrode of the present invention. However, the first substrate is not always made of an insulating material.

When this microbial sensor is used for the measurement of the concentration of matters in a sample solution, the sample solution is allowed to enter into the opening constituting a sample liquid accumulation portion by that amount which allows the sample solution to sufficiently come into contact with the membrane containing microorganism cells and the second conductor, and which, on the other hand, to prevent it from spilling over the frame disposed on the second conductor from the sample liquid accumulation portion. The sample solution osmoses into the membrane containing microorganism cells which is fixed on the first conductor which is inside of the opening of the second substrate, and then the microorganism metabolizes the matter in the sample solution within the membrane. This metabolism is associated with tansfer of the electrons occuring in the respiratory system of the microorganism, but in this sensor, instead of measuring directly this electrons transfer, a certain potential difference is applied between the first conductor to act as an electrode on which the membrane containing microorganism cells is fixed and the second conductor to act as a counter electrode and directly contact with a sample solution, so that the electrons easily transfer, and then an electric current flowing between both the electrodes is measured, thereby being capable of determining the concentration of the matter in the sample solution.

It is also possible to add a detachable or a fixed cover to the microbial sensor to prevent a sample liquid injected into the sample liquid accumulation portion from being dried during a measurement of the concentration of the matter. When the cover is fixed, it is necessary to add a passage to an appropriate place, for example, at the frame, by which the sample liquid can enter from outside of the microbial sensor into the sample liquid accumulation portion. Furthermore, in this case, the cover preferably has an air vent which faces on a part of the sample liquid accumulation portion, as same as the cover of the above described microbial sensor acting through capillary action. This is to facilitate smooth inflow of the sample liquid into the sample liquid accumulation portion.

According to the present invention, furthermore, taking advantages upon measurement of the concentration of matters in various sample liquids into consideration, there is provided a sample liquid collecting unit incorporating therein the respective microbial sensors described above.

In other words, the sample liquid collecting unit of the present invention is characterized by comprising a sample liquid sucking inlet, a sample liquid accumulation portion for storing sample liquid sucked through the sample liquid sucking inlet, and an aspiration pump portion for generating aspirating power, and incorporating a microbial sensor in the sample liquid accumulation portion.

Examples of this kind of sample liquid collecting unit may include a unit that comprises an apparatus having a sample liquid accumulation portion which can precisely suck a constant volume of sample liquid, such as a piston cylinder-type one like a syringe or a pipette-type one, and a microbial sensor incorporated therein.

According to the microbial sensor of the present invention, a certain potential difference is applied between an electrode on which the membrane containing microorganism cells is fixed and the counter electrode, and then an electric current flowing between both the electrodes is measured. For application of the potential difference and the measurement of the current, it is preferred to use a constant voltage generator, a potentiostat, or the like. Further, small-sized measuring instruments appropriate for the present purpose including the potentiostat or the like are commercially available. Thus, it is possible for the above mentioned sample liquid collecting unit of the present invention, or the like, to connect the microbial sensor with a small-sized measuring instrument such as a small potentiostat, and to incorporate it into the sample liquid collecting unit.

Further, an electron transport mediator (refer to as simply "mediator" hereinafter) is preferably added to a sample liquid, because it allows a higher sensitivity measurement. Otherwise, the mediator may be introduced into the interface with the sample liquid, such as the interior or surface of the membrane containing microorganism, a portion between the membrane containing microorganism and the electrode, or the like. It should be noted that when a mediator is used while being fixed on a microbial electrode, the mediator will elute into the sample liquid during measurement of the concentration of sample liquid. Therefore, with such microbial sensor, it is preferred to make the microbial sensor used one time disposable, or to replenish the sensor with fresh mediator after use for the next use.

The mediator facilitates, the electrons generating from the metabolism of the various matters by the microorganism to transfer to the electrode. The mediator may be composed of any materials, and is not limited to any specific materials as long as it facilitates the transfer of electrons from the microorganism to the electrodes. Examples of the mediator include pigments such as 1-methoxy-5-methylphenazinium methylsulfonate (1-M-PMS), 2,6-dichloroindophenol (DCIP), 9-dimethylaminobenzo-a-phenazoxonium chloride, methylene blue, indigotrisulfonic acid, phenosafranin, thionine, new methylene blue, 2,6-dichlorophenol, indophenol, azule B, N, N, N',N'-tetramethyl-p-phenylenediamine dihydrochloride, resorufine, safranine, sodium anthraquinone β-sulfonate, and indigo carmine; biological oxidation/reduction materials such as riboflavin, L-ascorbic acid, flavin adenine dinucleotide, flavin mononucleotide, nicotine adenine dinucleotide, lumichrome, ubiquinone, hydroquinone, 2,6-dichlorobenzoquinone, 2-methylbenzoquinone, 2,5-dihydroxybenzoquinone, 2-hydroxy-1,4-naphtoquinone, glutathione, peroxidase, cytochrom C and ferredoxin or their derivatives; and others such as Fe-EDTA, Mn-EDTA, Zn-EDTA, mesosulfate, 2,3,5,6-tetramethyl-p-phenylenediamine, potassium ferricyanide. The mediator preferably has a concentration of about 40 nM–100 mM, more preferably, about 10 μM–50 mM.

Of those compounds, 1-M-PMS, DCIP, potassium ferricyanide and 9-dimethylaminobenzo-α-phenazoxonium chloride are preferred.

Here, the method of measuring concentrations of matters contained in various sample solutions using the above-described respective microbial sensors will be briefly outlined below, taking as an example the measurement of BOD.

The measurement of BOD consists of drawing a standard curve using a standard sample, and then finding the BOD of a sample liquid from the value of electric current obtained with the use of the sample liquid. In other words, by using a buffer solution free of organic compounds, an electric current flowing between the working electrode, and the counter electrode or the reference electrode is measured, and the value of electric current is measured using different concentrations of standard sample to draw a standard curve. Subsequently, the measurement of electric current is conducted using a measuring sample or a measuring sample liquid diluted with the buffer solution in the same manner as in the above. These measurement values of electric currents are compared with the values of electric currents obtained using the standard sample, to thereby measure the BOD. Further, when the microbial sensor which has a mediator and a buffer solution stabilized on the membrane containing microorganism is used for the measurement, the sensor is directly immersed into the sample liquid, an electric current flowing between the working electrode (microbial electrode) and the counter electrode or the reference electrode is measured. The measurement values are compared with the values of electric currents obtained using a standard sample, to thereby measure the BOD.

The current flowing through the sensor depends on different parameters including the kind of microorganism, the contact area between the electrode and the microorganism membrane, the kind and the concentration of the mediator, the potential difference applied between the working electrode and the counter electrode, the concentration of BOD and the like. Therefore, these parameters may be determined as appropriate according to a given purpose after a preliminary experiment has been made.

When the BOD sensor of the present invention is immersed into a solution containing the organic compounds, those organic compounds are metabolized by the microorganism in the microorganism membrane of the sensor. Consequently, electrons transfer via the electron transport system. When the potential difference is applied between the working electrode and the counter electrode, electron transfers from the microorganism membrane to the working electrode. As a result, the current obtained is different from that given when electrons are not generated. The concentration of the organic compounds, that is, BOD can be measured by measuring the electric current.

BRIEF DESCRIPTION OF THE DRAWINGS

FIG. 1(a) is a perspective view and FIG. 1(b) is a sectional view thereof.

FIG. 2 is a diagram showing one embodiment of a microbial sensor according to the present invention; FIG. 2(a) is a perspective view and FIG. 2(b) is a sectional view thereof.

FIG. 3(a) is a perspective view and FIG. 3(b) is a sectional view thereof.

FIG. 6(a) is a assembling perspective view and FIG. 6(b) is a sectional view thereof.

FIG. 8 is a front view showing a example of the BOD-measuring system incorporating the microbial electrode according to the present invention.

FIG. 11 is a graph showing results of BOD measurements using the microbial electrode in which microorganism cells are immobilized with PVA-SbQ on an Omnimembrane substrate having a carbon electrode.

FIG. 12 is a graph showing results of BOD measurements using the microbial electrode in which microorganism cells are immobilized with glutaraldehyde on a gold-deposited Omnimembrane substrate.

FIG. 15 is a graph showing results of BOD measurements using the microbial electrode in which microorganism cells are immobilized with agarose on a gold-deposited polyester sheet substrate.

FIG. 16 is a graph showing results of BOD measurements using the microbial electrode in which microorganism cells are immobilized with agarose having a low melting-point on a gold-deposited Omnimembrane substrate.

FIG. 19 is a graph showing results of BOD measurements using the microbial electrode in which microorganism cells are immobilized with curdlan on a gold-deposited polyester sheet substrate.

FIG. 20 is a graph showing results of BOD measurements using the microbial electrode in which microorganism cells are immobilized with curdlan and glutaraldehyde on a gold-deposited Omnimembrane substrate.

FIG. 23 is a graph showing results of BOD measurements using the microbial electrode in which microorganism cells are immobilized with chitosan on a gold-deposited Omnimembrane substrate.

FIG. 24 is a graph showing results of BOD measurements using the microbial electrode in which microorganism cells are immobilized with ENT on a gold-deposited Omnimembrane substrate.

FIG. 25 is a graph showing a comparison of results of the BOD measurements obtained by 2-electrodes method (the microbial electrode and the counter electrode) and 3-electrodes method (the microbial electrode, the counter electrode and the reference electrode) applied for the microbial electrode in which microorganism cells are immobilized with PVA-SbQ on a gold-deposited Omnimembrane substrate.

FIG. 26 is a graph showing results of BOD measurements using the microbial electrode which incorporates a mediator with carboxymethyl cellulose.

FIG. 27 is a graph showing results of BOD measurements using the microbial electrode which incorporates a mediator with polyvinylpyrrolidone.

FIG. 28 is a graph showing results of glucose concentration measurements using a microbial electrode according to the present invention.

FIG. 29 is a graph showing results of glycerol concentration measurements using a microbial electrode according to the present invention.

FIG. 30 is a graph showing results of ethanol concentration measurements using a microbial electrode according to the present invention.

FIG. 33 is a graph showing results of acetic acid concentration measurements using a microbial electrode according to the present invention.

FIG. 34 is a graph showing results of sucrose concentration measurements using a microbial electrode according to the present invention.

DESCRIPTION OF THE PREFERRED EMBODIMENT

The present invention will be described specifically hereinafter.

EXAMPLE 1

Microbial Electrode and Microbial Sensor for Measurement of BOD

Figure 1:
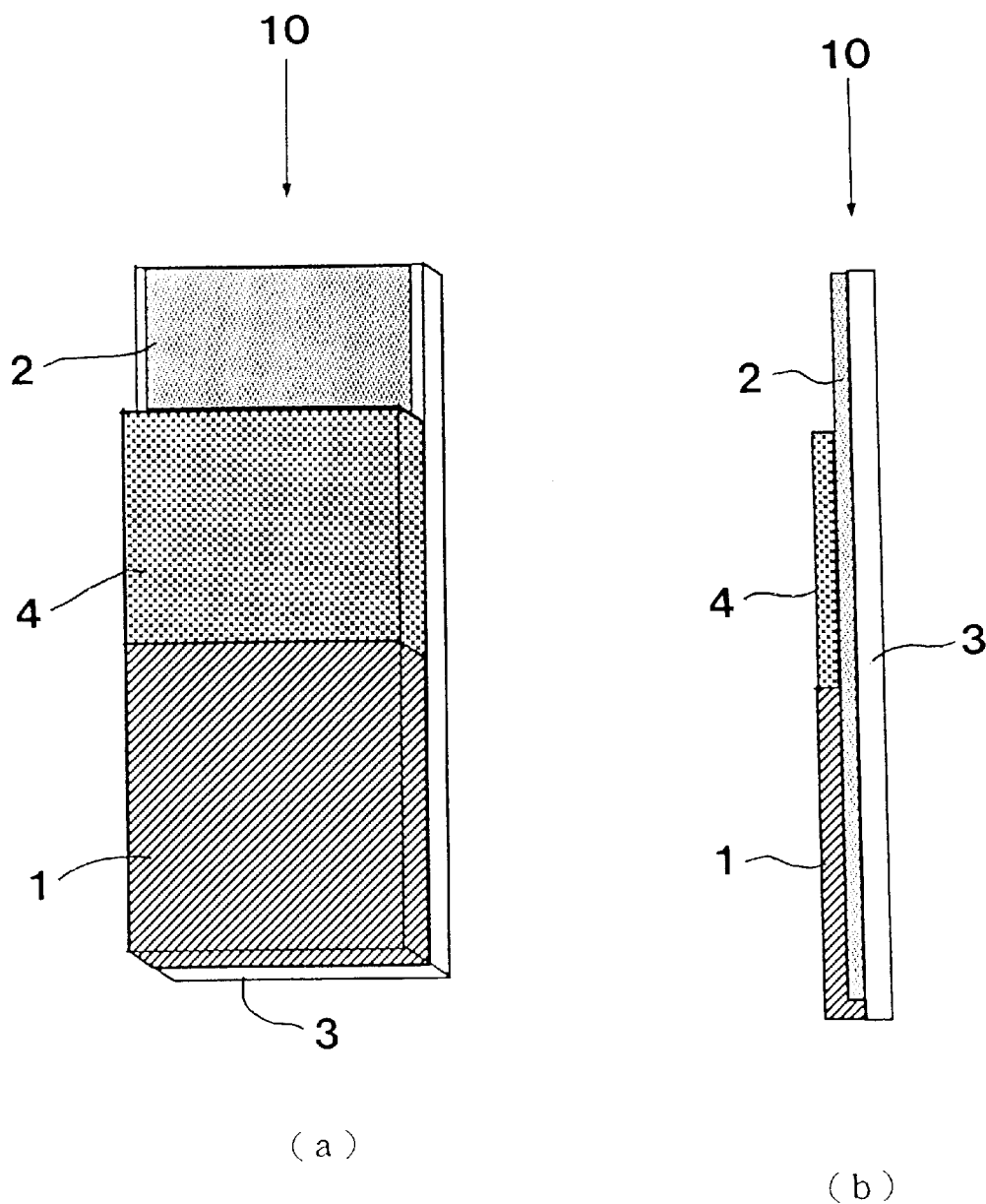
FIG. 1 is a diagram showing one embodiment of a microbial electrode according to the present invention.
Figure 3:
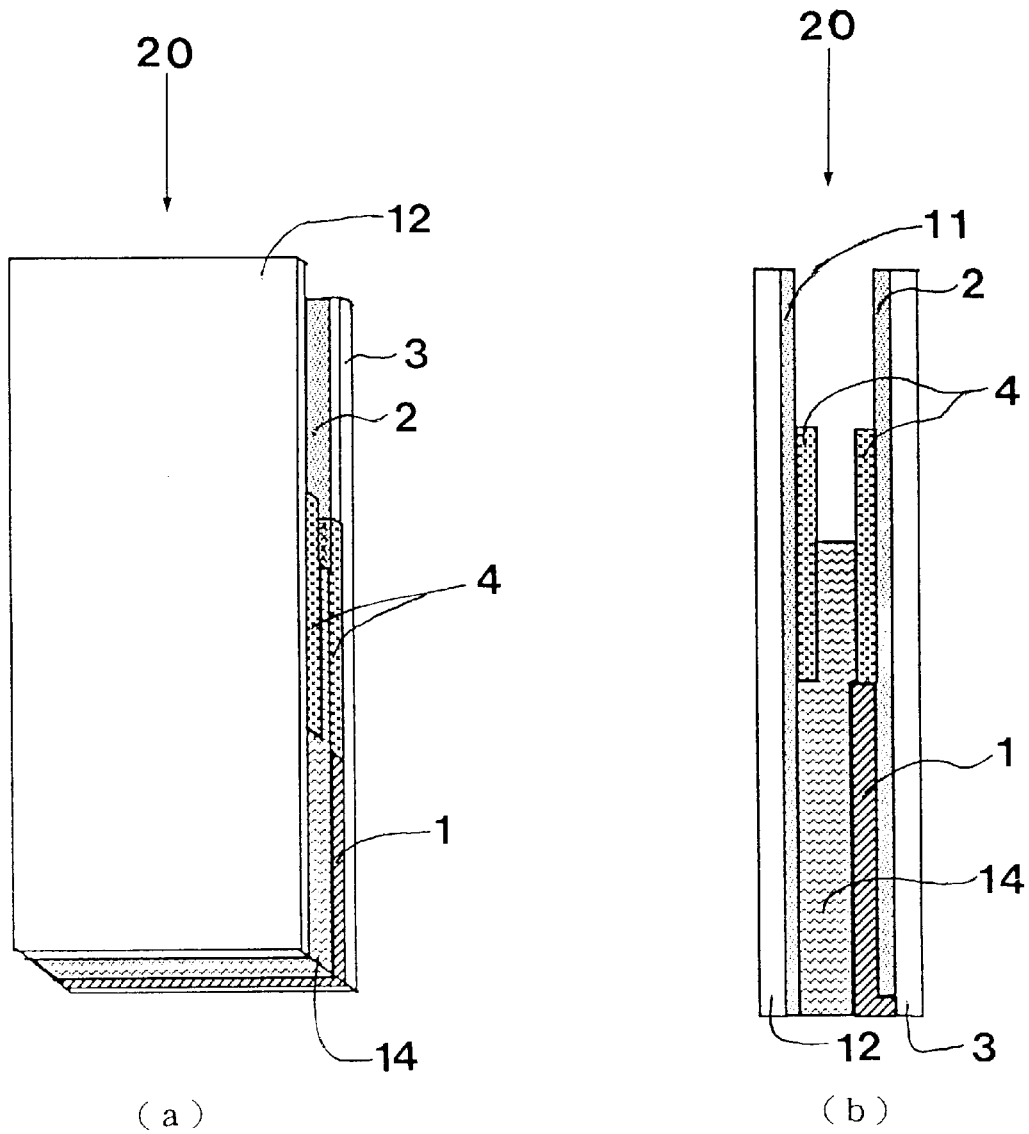
FIG. 3 is a diagram showing another embodiment of the microbial sensor according to the present invention.

Firstly, one example of a microbial electrode of the present invention which constitutes a BOD sensor and a BOD sensor incorporating this microbial electrode will be described on basis of FIGS. 1 to 3.

<Preparation of a microorganism suspension>

The *Pseudomonas fluorescens* IFO14160 strain was inoculated in 80 ml of a culture medium (pH 7.0) containing 0.3% $K_2HPO_4$, 0.1% $KH_2PO_4$, 0.03% $MgSO_4.7H_2O$, 0.5% ammonium sulfate, 0.001% L-glutamic acid and 0.1% yeast extract, and cultivated at 30° C. for 48 hours with shaking. The culture was centrifuged to separate the cells from the medium. The cells were washed with a buffer solution (0.05 M phosphate, pH 7.0), and suspended in the same buffer solution.

<Preparation of a microbial electrode>

On the central portion of one surface of a substrate of Omnimembrane 3 (Millipore, JGWP-14225) was evenly deposited gold 2 constituting an electrode. On this gold-deposited surface of Omnimembrane was coated with evenly a liquid which was produced after an appropriate amount of PVA-SbQ solution was added to the above cell suspension, so that when a microbial electrode was inserted into a sample liquid, the sample liquid might not come into contact with the gold electrode, and the whole was incubated in a dark place at 37° C. for three hours. Subsequently, a fluorescent lamp was irradiated to allow PVA-SbQ to undergo cross-linking reaction, to thereby form a membrane containing microorganism cells 1. If there were parts where the gold electrode might come into contact with the sample liquid, they were insulated with an epoxy resin 4. Thus, a microbial electrode 10 is prepared (FIG. 1).

<Preparation of a microbial sensor>

The following two kinds of microbial sensors were prepared by incorporating the above-described microbial electrode 10.

The first microbial sensor was first prepared after gold 11 to act as the counter electrode had been deposited evenly on the whole surface of above-described substrate of Omnimembrane 3 which was opposite to the surface where the membrane containing microorganism cells was fixed, and part of the gold-deposited surface was insulated with an epoxy resin 4 in order to adjust the contact area of the counter electrode with a sample liquid (FIG. 2).

The another type of microbial sensor will be described on basis of FIG. 3. The conductor to act as the counter electrode was made of gold 11 which was evenly deposited on one surface of a polyester film 12 to act as a substrate, and part of the gold-deposited surface was insulated with an epoxy resin 4 in order to adjust the contact area of the counter electrode with a sample liquid. Furthermore, a sponge 14 to act as a sample liquid holding member was inserted and fixed with an epoxy resin between the gold-deposited surface of the polyester film and the membrane containing microorganism cells of the microbial electrode 10 obtained above.

EXAMPLE 2

Another Embodiment of a Microbial Electrode

Figure 4:
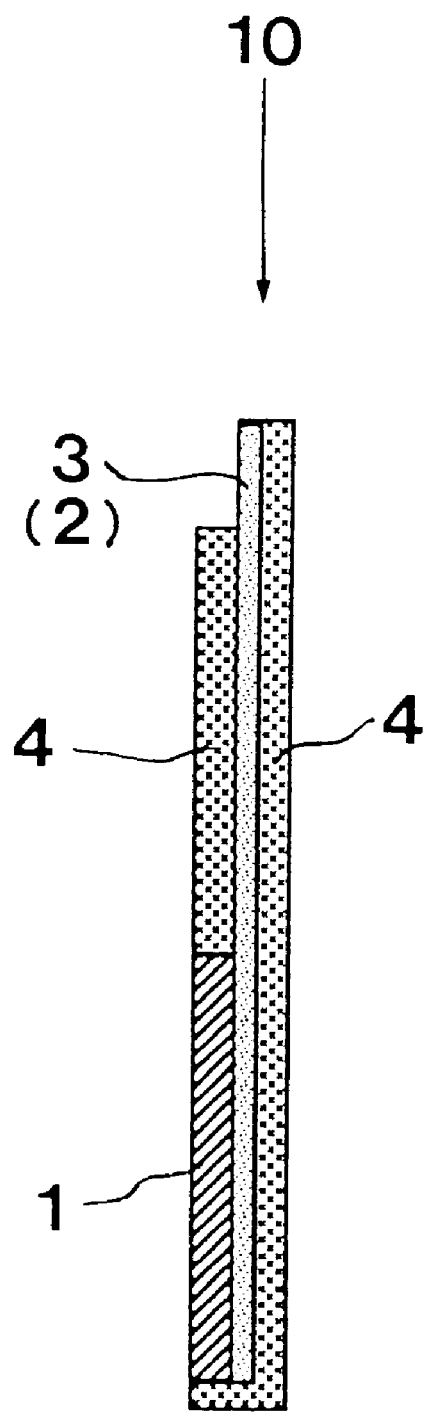
FIG. 4 is a sectional view showing another embodiment of the microbial electrode according to the present invention.

Another embodiment of a microbial electrode of the present invention will be described below on basis of FIG. 4.

A membrane containing microorganism 1 was allowed to form on one surface of a carbon film 3 to act as a substrate (this also acts as a conductor 2) in the same manner as in Example 1. The surface of the substrate which comes into contact with a sample liquid was insulated with an epoxy resin 4 except the portion on which the membrane containing microorganism was formed. Thus, a microbial electrode 10 was prepared.

EXAMPLE 3

Different Embodiment of a Microbial Sensor

Figure 5:
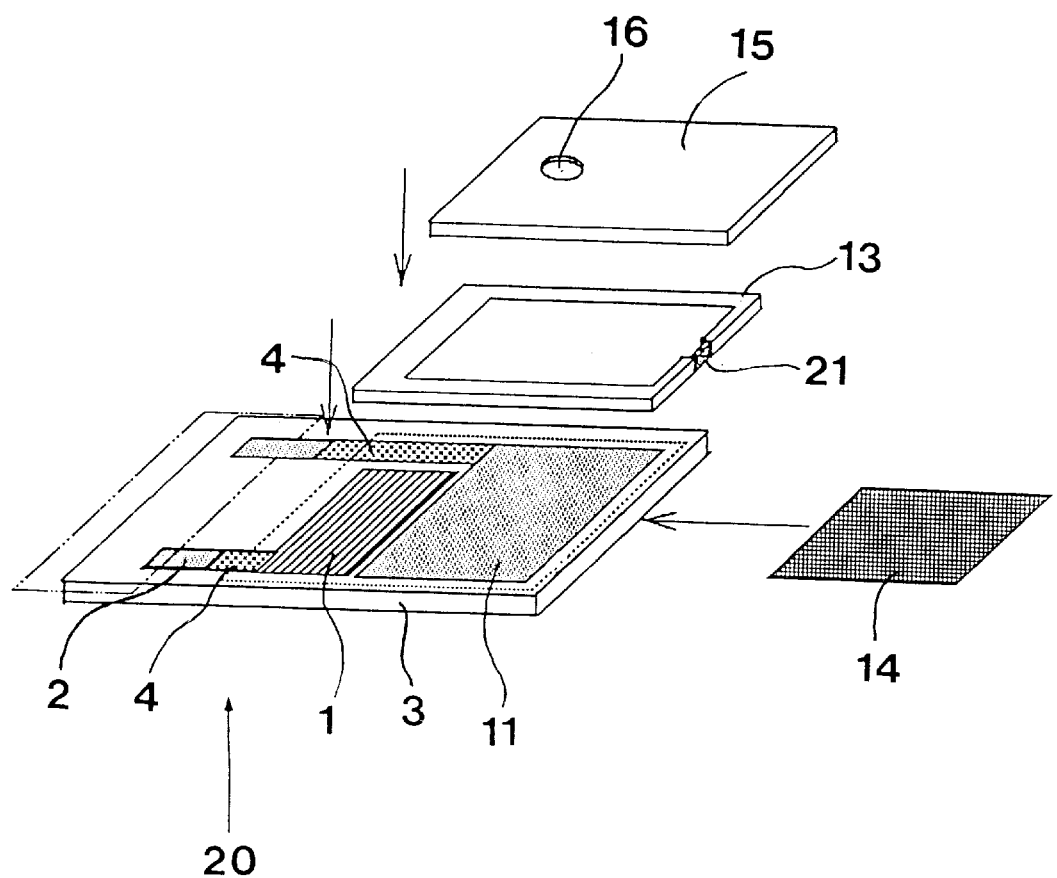
FIG. 5 is a exploded perspective view of different embodiment of the microbial sensor according to the present invention.

Different embodiment of a microbial sensor of the present invention will be described below on basis of FIG. 5.

Gold was deposited on two spots so as not to contact with each other on one surface of a substrate 3 made of polyester. On one of these gold-deposited portion, a membrane containing microorganism 1 was formed in the same manner as in Example 1, and the other was left as it was to act as a counter electrode 11. Further, within the gold-deposited portion 2 where the membrane containing microorganism was formed, any parts of it which might come into contact with a sample liquid was insulated with an epoxy resin 4. Furthermore, part of the gold-deposited portion to act as the counter electrode was insulated with an epoxy resin 4 in order to adjust the contact area of the counter electrode 11 with a sample liquid. The resulting product may be used as a microbial sensor when it is immersed into a sample liquid. The microbial sensor was further modified as follows so that it could automatically absorb the sample liquid through capillary action.

On the surface of the polyester substrate on which the membrane containing microorganism 1 and the counter electrode 11 were formed, a polyester spacer 13 having a sample liquid pouring inlet 21 with a filter was laminated to form a sample liquid holding portion, and a nylon mesh to act as a sample liquid holding member 14 was inserted into the sample liquid holding portion. Furthermore, a polyester cover 15 having an air vent 16 facing on a part of the sample liquid holding portion was laminated over the spacer 13 and the nylon mesh 14, thus a microbial sensor 20 utilizing a capillary action was prepared.

EXAMPLE 4

Further Different Embodiment of a Microbial Sensor

Figure 6:
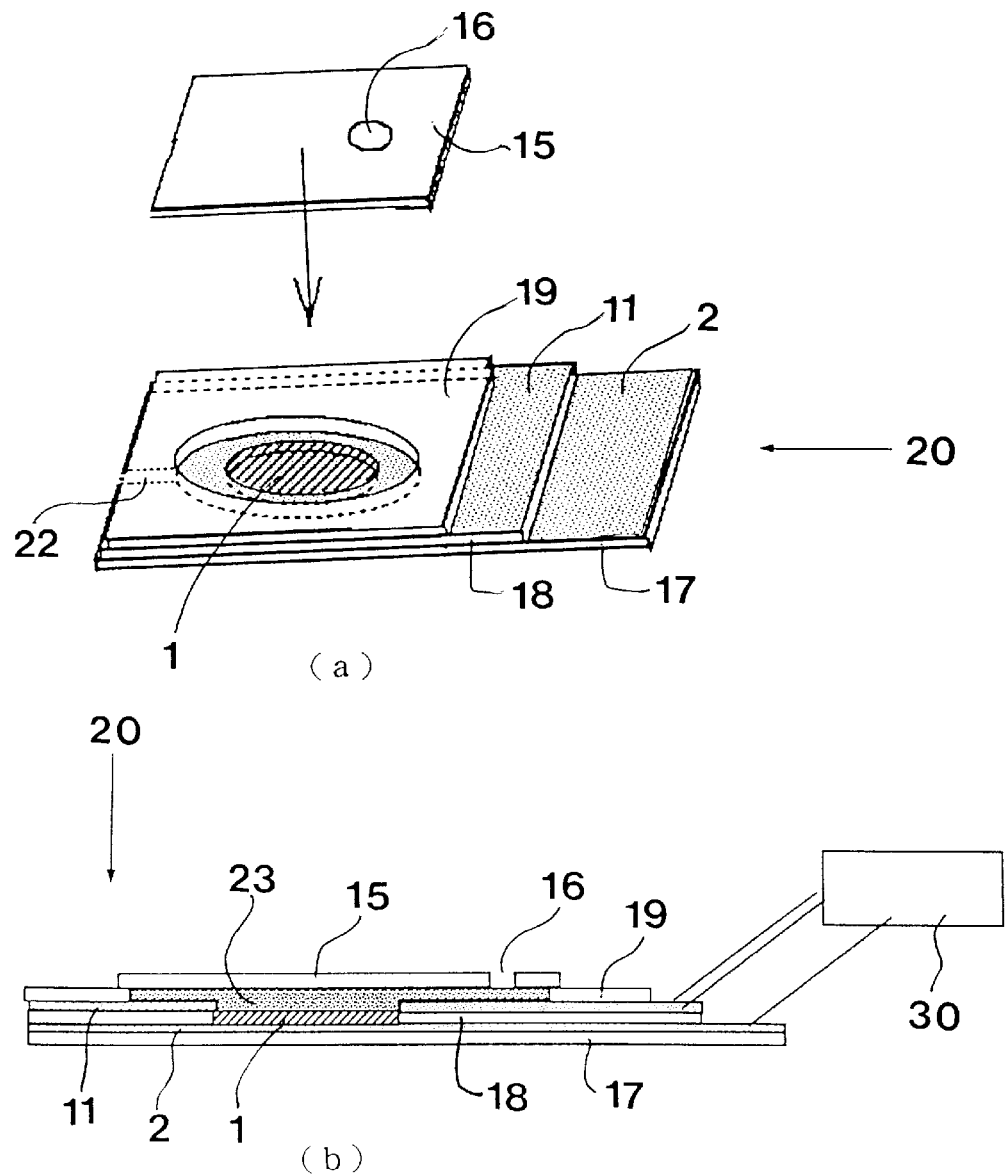
FIG. 6 is a diagram showing further different embodiment of the microbial sensor according to the present invention.

Further different embodiment of a microbial sensor will be described below on basis of FIG. 6.

On a surface of a first substrate 17 made of polyester was deposited with gold 2 to act as an electrode. On the gold-deposited surface of the first substrate 17, a second polyester substrate 18 having a round opening, which facing through the opening on a part of the gold-deposited surface was laminated. On a surface of the second substrate, a gold-deposited portion 11 to act as the counter electrode was formed in advance.

A membrane containing microorganism 1 was fixed on the gold-deposited surface on the first substrate and inside of the opening of the second substrate in the same manner as in Example 1. Furthermore, a polyester frame 19 having an opening to act as a sample liquid accumulation portion and a sample liquid injecting passage 22 for connecting outside of the microbial sensor to the sample liquid accumulation portion 23, and facing through the opening on the membrane containing microorganism cells 1 and a part of gold-deposited surface of the second substrate 18, was laminated thereupon. Still further, a polyester cover 15 having an air vent facing on a part of the sample liquid accumulation portion 23 was further laminated on the frame, to thereby prepare a microbial sensor 20.

EXAMPLE 5

Sample Liquid Collecting Unit

Figure 7:
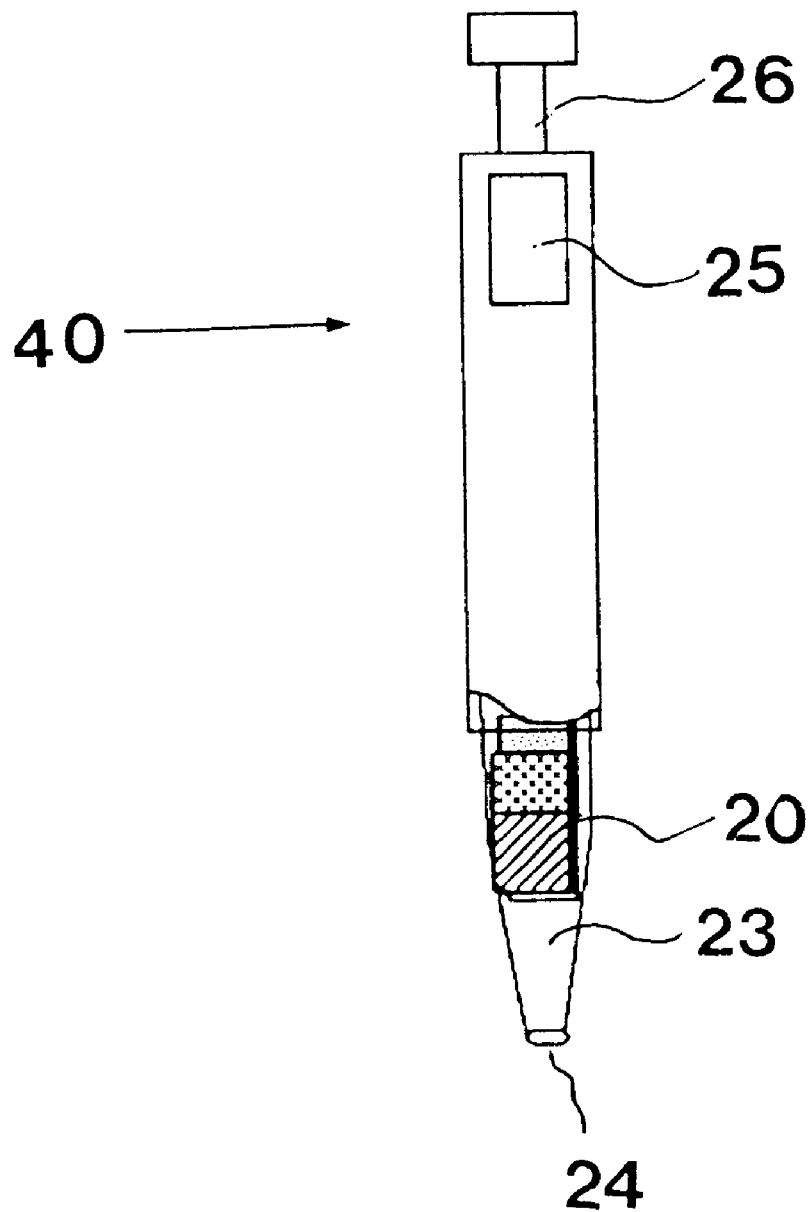
FIG. 7 is a partially sectioned side view showing one embodiment of a sample liquid collecting unit according to the present invention.

Into the body of a commercially available pipette (Pipettman, Gilson), a constant voltage generator was installed and the microbial sensor 20 obtained in Example 1 was connected and fixed thereto. A tip was attached at the tip of the microbial sensor 20, and on the side of the body, a current value display portion 25 for displaying the current measured by the constant voltage generator was further installed to provide a sample liquid collecting unit 40 (FIG. 7).

EXAMPLE 6

Example of BOD Measurement

Figure 9:
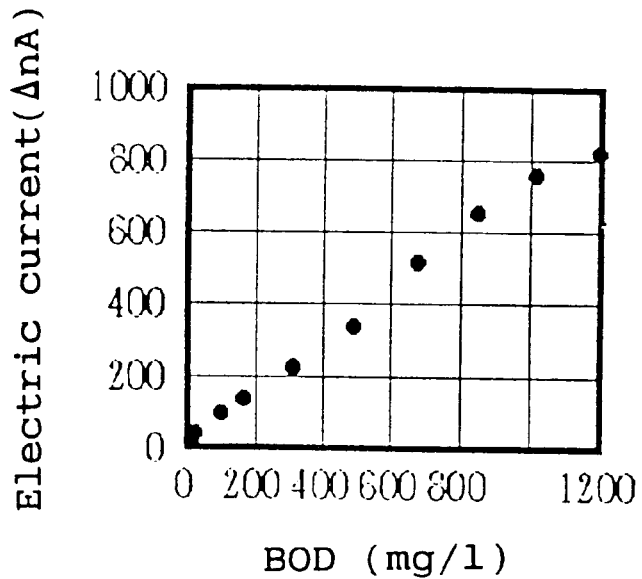
FIG. 9 is a graph showing results of BOD measurements using the microbial electrode in which microorganism cells are immobilized with PVA-SbQ on a gold-deposited Omnimembrane substrate.

By using the microbial electrode 10 as prepared in Example 1, BOD measurement was carried out with the following measurement system (FIG. 8). The above-described microbial electrode and a counter electrode (gold electrode) 11 were fixed to clips attached to a potentiostat 30, and the electrodes were immersed into a sample liquid tank 31 filled with a buffer solution to thereby prepare a BOD sensor. The gold counter electrode having its part insulated with an epoxy resin 4 to adjust its contact area with a sample liquid was used. A certain voltage was applied between the microbial electrode 10 and the counter electrode 11, and the flowing current was measured. Next, the standard BOD liquid (a mixed solution containing glucose and L-glutamic acid both at 150 mg/L (BOD at 220 mg/L), to be referred to as simply "BOD Standard liquid") was added together with a mediator (20 mM potassium ferricyanide (final concentration)), and the value of electric current was measured in the same manner as in the above. During the BOD measurement, the sample liquid was stirred with a magnetic stirrer 32. The measurements were fed to a computer 34. The results are shown in FIG. 9.

EXAMPLE 7

Various Immobilizing Methods and BOD Measurement

Further, the cell suspension of *Pseudomonas fluorescens* IFO14160 which was cultivated in the same manner as in Example 1 was immobilized on conductors fixed on various substrates, using various carriers as described below, to prepare different microbial electrodes. The BOD sensors comprising those microbial electrodes and counter electrodes were installed into the same measurement system with that in Example 6, and applied to measurement of BOD.

(1) BOD sensor incorporating cells immobilized with PVA-SbQ

Figure 10:
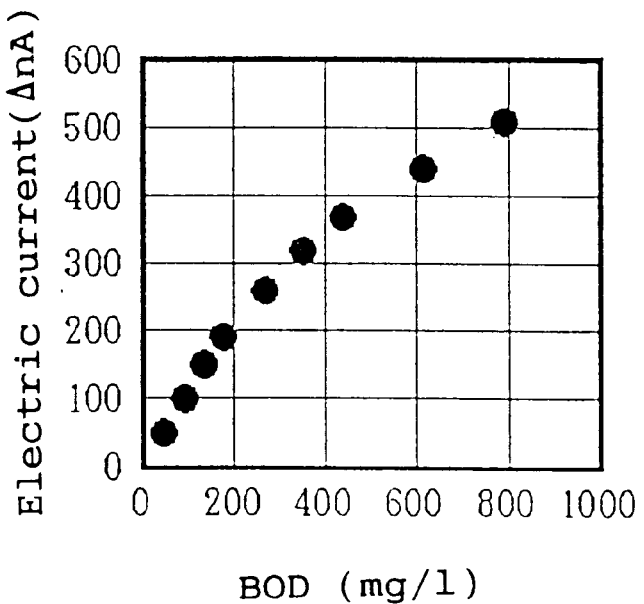
FIG. 10 is a graph showing results of BOD measurements using the microbial electrode in which microorganism cells are immobilized with PVA-SbQ on a gold-deposited polyester sheet substrate.

A microbial electrode was prepared in the same manner as in Example 1 except that a polyester sheet was employed instead of the Omnimembrane as a material of the substrate, and applied for the measurement of BOD. For the measurement of BOD, 0.01 M phosphate buffer solution (pH 7.0) as a buffer solution and 80 nM 1-M-PMS as a mediator were used. The results are shown in FIG. 10.

Further, another microbial electrode was prepared in the same manner as in Example 1 except that a carbon electrode was used instead of the gold electrode, and applied for the measurement of BOD. For the measurement of BOD, 0.01M phosphate buffer solution (pH 7.0) as a buffer solution and 10 mM potassium ferricyanide as a mediator were used. The results are shown in FIG. 11.

(2) Glutaraldehyde

A gold-deposited Omnimembrane to act as a substrate was the same as in Example 1. On this gold-deposited surface of Omnimembrane, a solution which was obtained after an appropriate amount of bovine serum albumin (BSA) was dissolved in the cell suspension obtained in Example 1 was coated evenly, in such a manner that, when the electrode was immersed into a sample liquid, the gold electrode might not come into direct contact with the sample liquid. The thus-obtained electrode was exposed to the vapor of a glutaraldehyde aqueous solution having a concentration of about 25% of for 20 minutes to form a microorganism containing membrane, and then rinsed three times with the phosphate buffer solution to prepare a microbial electrode.

This microbial electrode was applied for the measurement of BOD. For the measurement of BOD, 0.05 M phosphate buffer solution (pH 7.0) as a buffer solution and 20 mM potassium ferricyanide as a mediator were used. The results are shown in FIG. 12.

(3) PVA-SbQ+glutaraldehyde

The microbial electrode incorporating the gold-deposited polyester film substrate as obtained in above mentioned (1) was exposed to the vapor of a glutaraldehyde aqueous solution having a concentration of about 25% of for 20 minutes, and rinsed three times with the phosphate buffer solution to prepare a microbial electrode.

Figure 13:
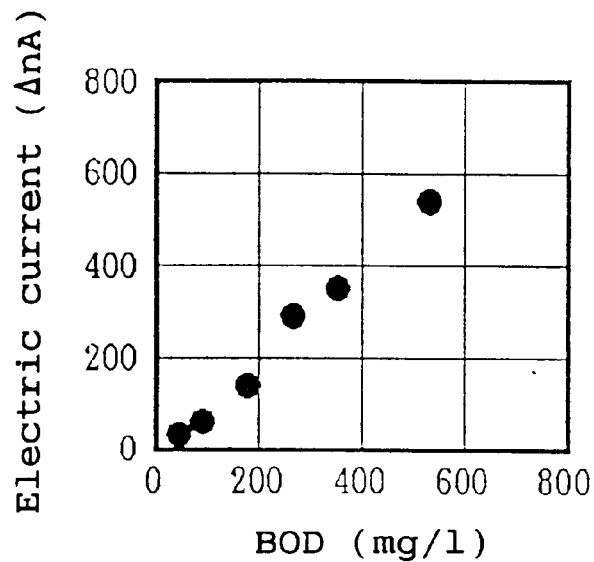
FIG. 13 is a graph showing results of BOD measurements using the microbial electrode in which microorganism cells are immobilized with PVA-SbQ and glutaraldehyde on a gold-deposited Omnimembrane substrate.

This electrode was applied for the measurement of BOD. For the measurement of BOD, 0.01 M phosphate buffer solution (pH 7.0) as a buffer solution and 80 nM 1-M-PMS as a mediator were used. The results are shown in FIG. 13.

(4) Agarose

Agarose was heat-dissolved to give an appropriate concentration (for example 2%), and was maintained at about 60° C., and the cell suspension obtained in Example 1 was added thereto and mixed. The resulting cell suspension in agarose solution was evenly coated onto two kinds of gold-deposited surfaces (gold-deposited polyester film substrate and gold-deposited Omnimembrane substrate) in such a manner that, when they were immersed into a sample liquid, the gold electrodes might not come into direct contact with the sample liquid, and they were cooled to prepare microbial electrodes.

Figure 14:
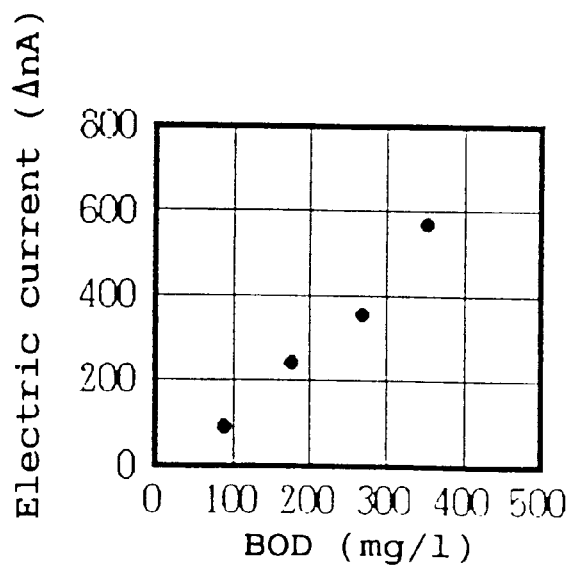
FIG. 14 is a graph showing results of BOD measurements using the microbial electrode in which microorganism cells are immobilized with agarose on a gold-deposited Omnimembrane substrate.

These two kinds of microbial electrodes were used for the measurement of BOD. For the BOD measurement with the electrode incorporating the gold-deposited Omnimembrane substrate, 0.05 M phosphate buffer solution (pH 7.0) as a buffer solution and 20 mM potassium ferricyanide as a mediator were used. The results are shown in FIG. 14. For the BOD measurement with the electrode incorporating the gold-deposited polyester film substrate, 0.01 M phosphate buffer solution (pH 7.0) as a buffer solution and 80 nM 1-M-PMS as a mediator were used. The results are shown in FIG. 15.

(5) Agarose having a low melting point

Agarose having a low melting point was heat-dissolved to give an appropriate concentration (for example 2%), and was maintained at about 40° C., and the cell suspension obtained in Example 1 was added thereto and mixed. The resulting cell suspension in the solution of agarose having a low melting point was evenly coated onto the gold-deposited surface of the gold-deposited Omnimembrane substrate in such a manner that, when it was immersed into a sample liquid, the gold electrode might not come into direct contact with the sample liquid. Then, it was cooled to prepare a microbial electrode.

The microbial electrode was used for the measurement of BOD. For the BOD measurement, 0.05 M phosphate buffer solution (pH 7.0) as a buffer solution and 20 mM potassium ferricyanide as a mediator were used. The results are shown in FIG. 16.

(6) Polyacrylamide

Polyacrylamide was heat-dissolved to give an appropriate concentration and the cell suspension obtained in Example 1 was added thereto and mixed. The resulting liquid was evenly coated onto the gold-deposited surface of the gold-deposited Omnimembrane substrate in such a manner that, when it was immersed into a sample liquid, the gold electrode might not come into direct contact with the sample liquid. Then, it was cooled to prepare a microbial electrode.

Figure 17:
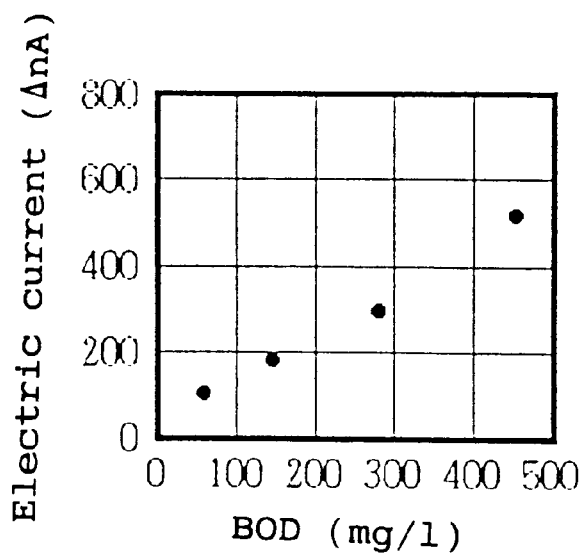
FIG. 17 is a graph showing results of BOD measurements using the microbial electrode in which microorganism cells are immobilized with polyacrylamide on a gold-deposited Omnimembrane substrate.

The microbial electrode was used for the measurement of BOD. For the BOD measurement, 0.05 M phosphate buffer solution (pH 7.0) as a buffer solution and 20 mM potassium ferricyanide as a mediator were used. The results are shown in FIG. 17.

(7) Curdlan

To 2% curdlan solution, the cell suspension obtained in Example 1 was added and mixed, and the mixture liquid was heated at 50 to 60° C. for about one minute to melt curdlan. The resulting liquid was evenly coated onto two kinds of gold-deposited surfaces (gold-deposited polyester film substrate and gold-deposited Omnimembrane substrate) in such a manner that, when they were immersed into a sample liquid, the gold electrodes might not come into direct contact with the sample liquid. Then, they were cooled and gelated, and dried at room temperature to prepare microbial electrodes.

Figure 18:
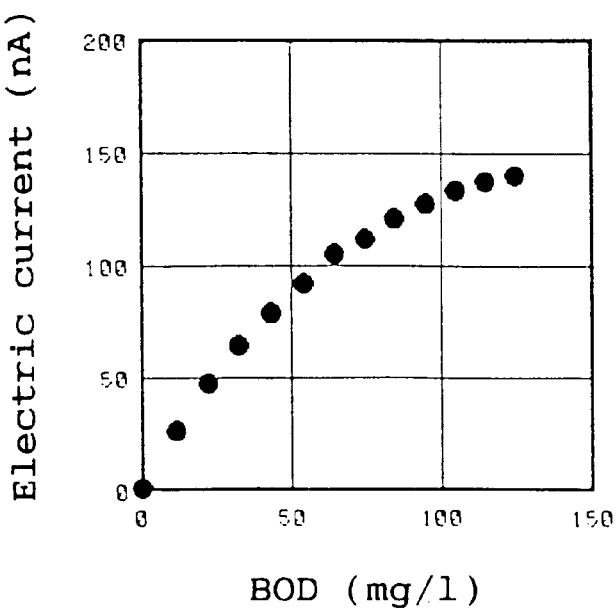
FIG. 18 is a graph showing results of BOD measurements using the microbial electrode in which microorganism cells are immobilized with curdlan on a gold-deposited Omnimembrane substrate.

These two kinds of microbial electrodes were used for the measurement of BOD. For the BOD measurement with the electrode incorporating the gold-deposited Omnimembrane substrate, 0.05 M phosphate buffer solution (pH 7.0) as a buffer solution and 200 $\mu$M 1-M-PMS as a mediator were used. The results are shown in FIG. 18. Further, for the BOD measurement with the electrode incorporating the gold-deposited polyester film substrate, 0.05 M phosphate buffer solution (pH 7.0) as a buffer solution and 20 $\mu$M 1-M-PMS as a mediator were used. The results are shown in FIG. 19.

(8) Curdlan+glutaraldehyde

The two kinds of microbial electrodes obtained in (6) described above were immersed into 2% glutaraldehyde aqueous solution and washed thoroughly, and then they were dried at room temperature.

Figure 21:
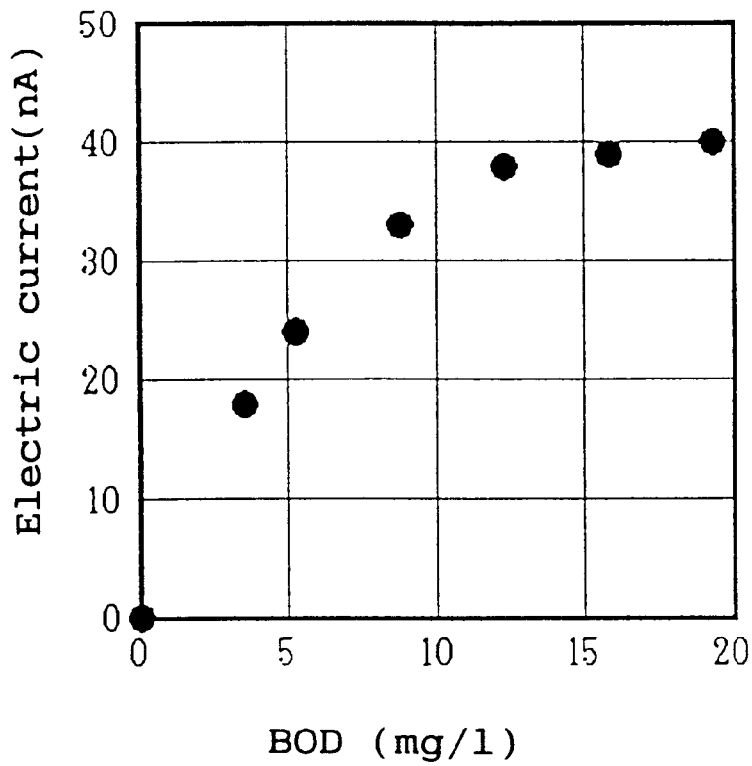
FIG. 21 is a graph showing results of BOD measurements using the microbial electrode in which microorganism cells are immobilized with curdlan and glutaraldehyde on a gold-deposited polyester sheet substrate.

These two kinds of microbial electrodes were used for the measurement of BOD. For the BOD measurement with the electrode incorporating the gold-deposited Omnimembrane substrate, 0.05 M phosphate buffer solution (pH 7.0) as a buffer solution and 200 μM 1-M-PMS as a mediator were used. The results are shown in FIG. 20. Further, for the BOD measurement with the electrode incorporating the gold-deposited polyester film substrate, 0.05 M phosphate buffer solution (pH 7.0) as a buffer solution and 20 μM 1-M-PMS as a mediator were used. The results are shown in FIG. 21.

(9) Carrageenan

To 1.5% carrageenan solution, the cell suspension obtained in Example 1 was added and mixed, and the mixture liquid was evenly coated onto the gold-deposited surface of the gold-deposited Omnimembrane substrate in such a manner that, when it was immersed in a sample liquid, the gold electrode might not come into direct contact with the sample liquid. Then, it was cooled and gelated. Thereafter, the product was immersed into 2% potassium chloride solution for several hours, and dried at room temperature to prepare a microbial electrode.

Figure 22:
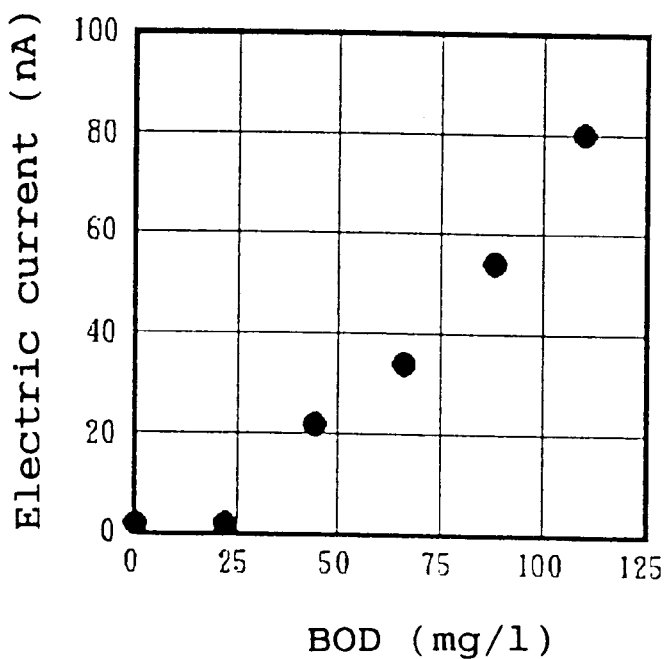
FIG. 22 is a graph showing results of BOD measurements using the microbial electrode in which microorganism cells are immobilized with carrageenan on a gold-deposited Omnimembrane substrate.

The microbial electrode was used for the measurement of BOD. For the BOD measurement, 0.05 M phosphate buffer solution (pH 7.0) as a buffer solution and 5 mM potassium ferricyanide as a mediator were used. The results are shown in FIG. 22.

(10) Chitosan

To a chitosan solution which was prepared after 1–8% chitosan was dissolved into 1–2% acetic acid aqueous solution, the cell suspension obtained in Example 1 was added and mixed, and the mixture liquid was evenly coated onto the gold-deposited surface of the gold-deposited Omnimembrane substrate in such a manner that, when it was immersed into a sample liquid, the gold electrode might not come into direct contact with the sample liquid. Then, it was dried at room temperature to prepare a microbial electrode.

The microbial electrode was used for the measurement of BOD. For the BOD measurement, 0.05 M phosphate buffer solution (pH 7.0) as a buffer solution and 20 mM potassium ferricyanide as a mediator were used. The results are shown in FIG. 23.

(11) Photo-setting resin 1 g of photo-setting resin (ENT-2000, Kansai Paint) and 0.01 g of photo-polymerization inducer were mixed, and 0.5 g of the cell suspension obtained in Example 1 was added thereto and mixed. The mixture liquid was evenly spread onto the gold-deposited surface of the gold-deposited Omnimembrane substrate in such a manner that, when it was immersed into a sample liquid, the gold electrode might not come into direct contact with the sample liquid. Then, it was covered with a polypropylene film so that it might not contact with air, and light was irradiated for polymerization. Thereafter, the polypropylene film was removed to prepare a microbial electrode.

The microbial electrode was used for the measurement of BOD. For the BOD measurement, 0.05 M phosphate buffer solution (pH 7.0) as a buffer solution and 20 mM potassium ferricyanide as a mediator were used. The results are shown in FIG. 24.

From above results it is obvious that the BOD sensor of the present invention may be applied for the measurement of BOD regardless of the method of immobilizing the microorganism cells onto the metal electrode.

EXAMPLE 8

Comparison of 2-Electrodes Method and 3-Electrodes Method

A microbial electrode was prepared by immobilizing *Pseudomonas fluorescens* IFO14160 onto a gold-deposited Omnimembrane substrate with PVA-SbQ in the same manner as in Example 1, and this microbial electrode was combined with the counter electrode in 2-electrodes method, or with the counter electrode and the reference electrode in 3-electrodes method to measure BOD. Then they were used for the measurement of BOD.

In 2-electrodes method, the measurement was carried out in the same manner as in Example 6 while in 3-electrodes method, the measurement was carried out in the same manner as in Example 6 except that an Ag/AgCl electrode was used as a reference electrode. For these BOD measurements, 0.05 M phosphate buffer solution (pH 7.0) as a buffer solution and 20 mM potassium ferricyanide as a mediator were used. The results are shown in FIG. 25.

From this result it is obvious that it may be sufficiently available to measure the BOD whether with 2-electrodes method using only the microbial electrode and the counter electrode, or with 3-electrodes method using the microbial electrode, the counter electrode and the reference electrode without the large difference of the results of the measurement between both the methods.

EXAMPLE 9

Microbial Electrode Containing a Mediator

A microbial sensor was prepared which having a microbial electrode in which *Pseudomonas fluorescens* IFO14160 was immobilized on a gold-deposited polyester substrate with PVA-SbQ in the same manner as in Example 4, except that, after the membrane containing microorganism was formed, that membrane containing microorganism was allowed to contain a mediator with the following method. Thus, a disposable, mediator containing microbial sensor was obtained.

(1) Method for containing a mediator with carboxymethyl cellulose

Potassium ferricyanide as a mediator was dissolved in an appropriate amount of 1% concentration of carboxymethyl cellulose solution, spread onto a membrane containing microorganism, and dried so that the mediator might be incorporated into the membrane containing microorganism.

(2) Method for cntaining a mediator with polyvinylpyrrolidone

Potassium ferricyanide as a mediator was dissolved in an appropriate amount of about 10% concentration of polyvinylpyrrolidone solution, spread onto a membrane containing microorganism, and dried so that the mediator might be incorporated into the membrane containing microorganism.

Mediator containing microbial sensors were prepared in the same manner as in Example 4 except that the membrane containing microorganism was allowed to contain the mediator by the above two methods. The sensors were applied for the measurement of BOD with the following method.

BOD standard liquid and a buffer solution (0.05 M phosphate buffer solution, pH 7.0) were so mixed as to prepare solutions with different BOD concentrations. One of the BOD buffer solution of them was injected into the sample liquid accumulation portion of one of the microbial sensor prepared by the method (1), and the value of electric current was measured. When this kind of measurement with the mediator containing microorganism membrane is used for the measurement of BOD, the mediator is fixed on the electrode, and after a sample liquid is injected into the sensor, the mediator will dissolve into the sample liquid. Therefore, once the sensor is used, it can not be used for succeeding measurements (or the mediator must be replenished for succeeding measurements). Then, a different sensor prepared, however, by the same method (1) was applied for the measurement of BOD of a BOD buffer solution having a different concentration from the foregoing. The same operation was repeated each time a fresh BOD buffer solution with a different concentration was subjected to measurement. Finally, all the BOD buffer solutions with different concentrations were measured of their values of electric current of BOD buffer solutions, and the results are shown in FIG. 26.

In the same manner as in the above, the microbial sensors prepared by the method (2) were applied for the measurement of values of the electric current of BOD buffer solutions with different concentrations. The results are shown in FIG. 27.

From above results it is obvious that the use of the microbial electrode incorporating a mediator gives the same results of the measurments as derived from a sample liquid supplemented with the mediator.

EXAMPLE 10

Measurement of the Concentration of Matters Contained in Various Sample Liquids

Microbial electrodes were prepared in the same manner as in Example 1, to measure the concentration of the matters as listed in Table 1 with the microorganisms as listed in Table 1.

TABLE 1

| Matters to be measured | Microorganisms |
| --- | --- |
| Glucose | Gluconobacter suboxydans IFO3172 |
| Glycerose | Pseudomonas fluorescens IFO14160 |
| Ethanol | Gluconobacter rubiginosus IFO3244 |
| L-glutamic acid | Pseudomonas fluorescens IFO14160 |
| Maltose | Pseudomonas pseudomallei ATCC15682 |
| Acetic acid | Bacillus subtilus IFO13719 |
| Sucrose | Pseudomonas caryophylli IFO13591 |
| S. starch | Pseudomonas putida IFO14164 |

The cultivation of microorganisms were made as follows. The same method was employed as in Example 1 for the cultivation of Pseudomonas fluorescens IFO14160.

For the cultivation of Gluconobacter suboxydans IFO3172, Gluconobacter rubiginosus IFO3244 and Pseudomonas caryophylli IFO13591, the ingredients as listed in Table 2 were mixed with purified water to 1 L to prepare a culture medium (pH 7.0). To each of 100 ml of this medium, above microorganisms were inoculated respectively, and cultivated at 30° C. for 24 hours with shaking. The each culture was centrifuged to separate the cells from the medium. The cells were washed with a buffer solution (0.05 M phosphate, pH 7.0), and suspended in the same buffer solution.

TABLE 2

| Ingredient | Content (g) |
| --- | --- |
| Potato extract | 200 |
| Condensed yeast | 30 |
| Liver extract | 25 |
| Meat extract | 5 |
| Thioglycolate medium dehydrated | 10 |
| Glucose | 5 |
| Glycerol | 15 |
| Calcium carbonate | 15 |

For the cultivation of Pseudomonas putida IFO14164, the ingredients as listed in Table 2 excluding calcium carbonate were mixed with purified water to 1 L to prepare a culture medium (pH 7.0). To 100 ml of this medium, the microorganism was inoculated, and cultivated at 30° C. for 24 hours with shaking. The culture was centrifuged to separate the cells from the medium. The cells were washed with a buffer solution (0.05M phosphate, pH 7.0), and suspended in the same buffer solution.

For the cultivation of Bacillus subtilus IFO13719, the ingredients as listed in Table 3 were mixed with purified water to 1 L to produce a culture medium (pH 7.0). To 100 ml of this medium, the microorganism was inoculated, and cultivated at 30° C. for 24 hours with shaking. The culture was centrifuged to separate the cells from the medium. The cells were washed with a buffer solution (0.05 M phosphate, pH 7.0), and suspended in the same buffer solution.

TABLE 3

| Ingredient | Content (g) |
| --- | --- |
| Peptone | 10 |
| Yeast extract | 5 |
| Liver extract | 25 |
| Glucose | 3 |
| Glycerol | 15 |
| Sodium chloride | 3 |

For the cultivation of Pseudomonas pseudomallei ATCC15682, the ingredients as listed in Table 4 were mixed with purified water to 1 L to prepare a culture medium (pH 7.0). To 100 ml of this medium, the microorganism was inoculated, and cultivated at 37° C. for 24 hours with shaking. The culture was centrifuged to separate the cells from the medium. The cells were washed with a buffer solution (0.05 M phosphate, pH 7.0), and suspended in the same buffer solution.

TABLE 4

| Ingredient | Content (g) |
| --- | --- |
| Beef extract | 3 |
| Peptone | 10 |
| Sodium chloride | 5 |
| Glycerol | 40 |

Microbial electrodes were prepared in the same manner as in Example 1, by immobilizing the microorganisms cultivated as above on gold-deposited Omnimembranes with PVA-SbQ, to measure the concentration of matters contained in various sample liquids below.

(1) Measurement of glucose concentration

The microbial electrode incorporating Gluconobacter suboxydans IFO3172 cultivated as described above was applied to the same measurement system as used in Example 6 to measure the concentration of glucose. First, a certain voltage was applied between the microbial electrode and the counter electrode dipped in a sample liquid tank containing a mediator-supplemented (20 mM potassium ferricyanide) buffer solution, and the value of electric current flowing therebetween was measured. Then, a standard liquid (a glucose solution comprising 100 mg of glucose/10 ml) was added and the value of electric current was measured in the same manner. The result was recorded with a recorder. The results are shown in FIG. 28.

(2) Measurement of glycerol concentration

The microbial electrode incorporating Pseudomonas fluorescens IFO14160 cultivated as described above was applied to the same measurement system as used in Example 6 to measure the concentration of glycerol. First, a certain voltage was applied between the microbial electrode and the counter electrode dipped in a sample liquid tank containing a mediator-supplemented (20 mM potassium ferricyanide) buffer solution, and the resulting electric current was measured. Then, a standard liquid (a glycerol solution comprising 100 mg of glycerol/10 ml) was added and electric current was measured in the same manner. The result was recorded with a recorder. The results are shown in FIG. 29.

(3) Measurement of ethanol concentration

The microbial electrode incorporating *Gluconobacter rubiginosus* IFO3244 cultivated as described above was applied to the same measurement system as used in Example 6 to measure the concentration of ethanol. First, a certain voltage was applied between the microbial electrode and the counter electrode dipped in a sample liquid tank containing a mediator-supplemented (20 mM potassium ferricyanide) buffer solution, and the resulting electric current was measured. Then, a standard liquid (an ethanol solution comprising 100 mg of ethanol/10 ml) was added and electric current was measured in the same manner. The result was recorded with a recorder. The results are shown in FIG. 30.

(4) L-glutamic acid

Figure 31:
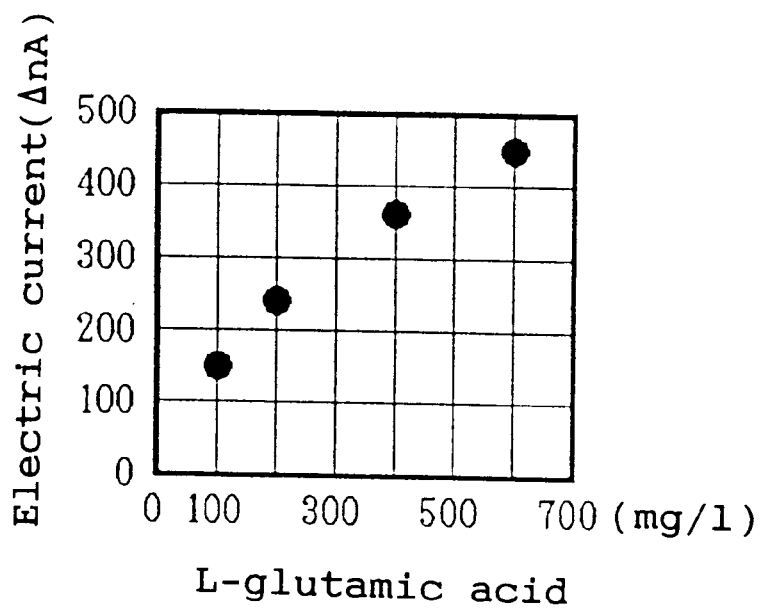
FIG. 31 is a graph showing results of L-glutamic acid concentration measurements using a microbial electrode according to the present invention.

The microbial electrode incorporating *Pseudomonas putida* IFO14164 cultivated as described above was applied to the same measurement system as used in Example 6 to measure the concentration of L-glutamic acid. First, a certain voltage was applied between the microbial electrode and the counter electrode dipped in a sample liquid tank containing a mediator-supplemented (20 mM potassium ferricyanide) buffer solution, and the resulting electric current was measured. Then, a standard liquid (a L-glutamic acid solution comprising 100 mg of L-glutamic acid/10 ml) was added and electric current was measured in the same manner. The result was recorded with a recorder. The results are shown in FIG. 31.

(5) Maltose

Figure 32:
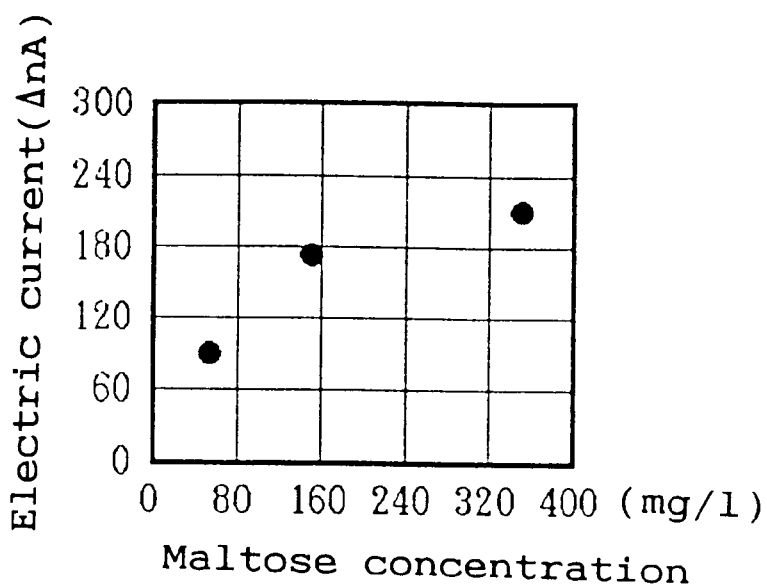
FIG. 32 is a graph showing results of maltose concentration measurements using a microbial electrode according to the present invention.

The microbial electrode incorporating *Pseudomonas pseudomallei* ATCC15682 cultivated as described above was applied to the same measurement system as used in Example 6 to measure the concentration of maltose. First, a certain voltage was applied between the microbial electrode and the counter electrode dipped in a sample liquid tank containing a mediator-supplemented (20 mM potassium ferricyanide) buffer solution, and the value of electric current flowing therebetween was measured. Then, a standard liquid (a maltose solution comprising 100 mg of maltose/10 ml) was added and electric current was measured in the same manner. The result was recorded with a recorder. The results are shown in FIG. 32.

(6) Acetic acid

The microbial electrode incorporating *Bacillus subtilus* IFO13719 cultivated as described above was applied to the same measurement system as used in Example 6 to measure the concentration of acetic acid. First, a certain voltage was applied between the microbial electrode and the counter electrode dipped in a sample liquid tank containing a mediator-supplemented (20 mM potassium ferricyanide) buffer solution, and the value of electric current flowing therebetween was measured. Then, a standard liquid (an acetic acid solution comprising 100 mg of acetic acid/10 ml) was added and electric current was measured in the same manner. The result was recorded with a recorder. The results are shown in FIG. 33.

(7) Sucrose

The microbial electrode incorporating *Pseudomonas caryophylli* IFO13591 cultivated as described above was applied to the same measurement system as used in Example 6 to measure the concentration of sucrose. First, a certain voltage was applied between the microbial electrode and the counter electrode dipped in a sample liquid tank containing a mediator-supplemented (20 mM potassium ferricyanide) buffer solution, and the value of electric current flowing therebetween was measured. Then, a standard liquid (a sucrose solution comprising 100 mg of sucrose/10 ml) was added and electric current was measured in the same manner. The result was recorded with a recorder. The results are shown in FIG. 34.

(8) S. starch

Figure 35:
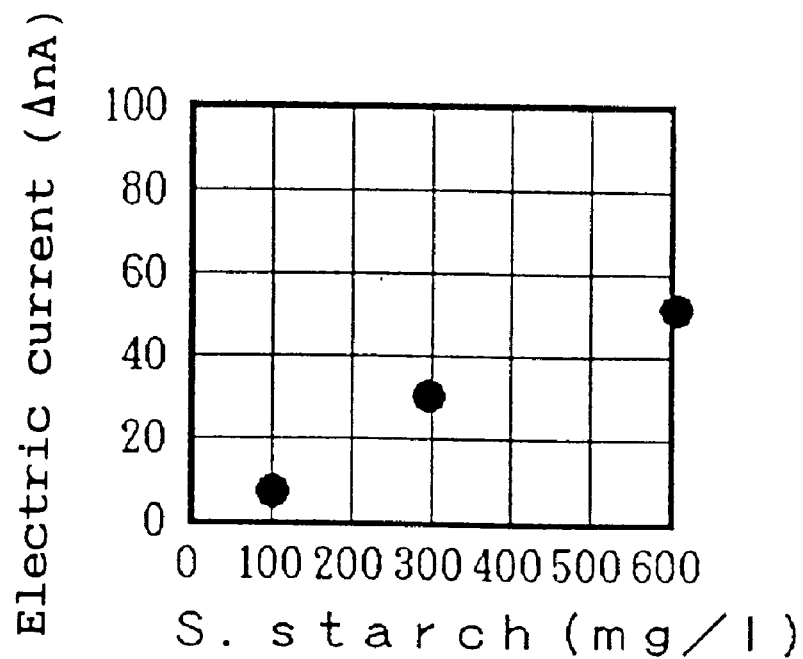
FIG. 35 is a graph showing results of S. starch concentration measurements using a microbial electrode according to the present invention.

The microbial electrode incorporating *Pseudomonas putida* IFO14164 cultivated as described above was applied to the same measurement system as used in Example 6 to measure the concentration of S. starch. First a certain voltage was applied between the microbial electrode and the counter electrode dipped in a sample liquid tank containing a mediator-supplemented (20 mM potassium ferricyanide) buffer solution, and the value of electric current flowing therebetween was measured. Then, a standard liquid (a S. starch solution comprising 100 mg of S. starch/10 ml) was added and electric current was measured in the same manner. The result was recorded with a recorder. The results are shown in FIG. 35.

From above results, it is obvious that according to the present invention it can be profitably to measure of the concentration of various matters contained in various sample liquids, besides BOD.

Industrial Applicability

The microbial electrode and the microbial sensor of the present invention allow the measurement even in a solution poor in dissolved oxygen, and enables direct measurement of the concentration of matters in a solution without resorting to oxygen electrodes, thereby being capable of down sizing. Accordingly, the present invention is able to provide a microbial sensor with reduced cost as production, which is disposable and free from reduced precision in measurement due to deteriorated microorganisms after long use.

We claim:

1. A microbial sensor for measuring a chemical or biological component present in a solution, comprising:
    (a) a microbial electrode comprising:
        an electric conductor;
        a microorganism cell layer fixed on and electronically contacted with the electric conductor to detect transfer of electrons generated by the microorganism cells when metabolizing the chemical or biological component; and
        an insulating layer which insulates the electric conductor from the solution when in use;
    (b) a counter electrode which is in contact with the solution when used;
    (c) a support having two faces insulated from each other, wherein the electric conductor of the microbial electrode is fixed on one of the faces to sandwich said electric conductor between said microorganism cell layer and said support, and the counter electrode is fixed on the other face of said support;
    (d) a generator of electric potential which generates an electric potential between the counter electrode and the microbial electrode to facilitate transfer of electrons therebetween generated by the microorganism cells; and
    (e) a detector for measuring the electric current passing between the counter electrode and the microbial electrode; whereby the chemical or biological component is measured based on a predetermined correlation between the measured electric current and the amount of electrons transferred by the microorganism cells when metabolizing the chemical or biological component.

2. The microbial sensor of claim 1, wherein said microorganism cells are procaryotic cells selected from the group consisting of; *E. coli,* Bacillus, Gluconobacter, Pseudomonas, and Actinomycetes.

3. The microbial sensor of claim 1, wherein said microorganisms are included into a gel membrane, photo-setting resin membrane, or a polyacrylamide membrane, or a polymer membrane.

4. The microbial sensor of claim 3, wherein said gel membrane is selected from the group consisting of; an alginate gel membrane, a carrageenan gel membrane, an agarose gel membrane, a cudlan gel membrane and an achitosan gel membrane.

5. The microbial sensor of claim 3, wherein said photo-setting resin membrane is a photo crosslinkable polyvinyl alcohol membrane.

6. The microbial sensor of claim 1, wherein said electric conductor is platinum, gold, silver, graphite, or carbon.

7. The microbial sensor of claim 1 further comprising a mediator for facilitating the transfer of electrons generating from the metabolism of the various chemical or biological components to the electrode.

8. The microbial sensor of claim 7, wherein said mediator is selected from the group consisting of pigments, biological oxidation/reduction materials, and metal EDTA compounds.

9. The microbial sensor of claim 8, wherein the pigments are selected from the group consisting of 1-methoxy-5-methylphenaxinium methylsulfonate, 2,6-dichloroindophenol, 9-dimethylaminobenzo-a-phenazoxonium chloride, methylene blue, indigotrisulfonic acid, phenosafranin, thionine, new methylene blue, 2,6-dichlorophenol, indophenol, azule B, N,N,N',N'-tetramethyl-p-phenylenediamine dihyrochloride, resorufine, safianine, sodium anthraquinone β-sulfonate, and indigo carmine.

10. The microbial sensor of claim 8, wherein said biological oxidation/reduction materials are selected from the group consisting of riboflavin, L-ascorbic acid, flavin adenine dinucleotide, flavin mononucleotide, nicotine adenine dinucleotide, lumichrome, ubiquinone, hyroquinone, 2,6-dichlorobenzoquinone, 2-methylbenzoquinone, 2,5-dihyroxybenzoquinone, 2-hydroxy-1,4-naphtoquinone, glutathione, peroxidase, cytochrome C and ferredoxin.

11. The microbial sensor of claim 8, wherein said metal EDTA compounds are selected from the group consisting of Fe-EDTA, MN-EDTA, Zn-EDTA.

12. The microbial sensor of claim 7 wherein said mediator has a concentration of 40 nM to 100 mM.

13. The microbial sensor of claim 12 wherein said mediator has a concentration of 10 $\mu$M to 50 mM.

14. The microbial sensor of claim 1 further comprising a reference electrode used to set the potential of the microbial electrode.

15. The microbial sensor of claim 1 further comprising additional microbial electrodes allowing for the synchronous measurement of a plurality of chemical or biological components.

16. The microbial sensor according to claim 1, which is incorporated in a sample liquid collecting unit comprising: a sample liquid-sucking inlet; a liquid accumulation portion for storing sample liquid sucked through the sample liquid-sucking inlet; and an aspiration pump portion for generating an aspirating power, wherein the microbial sensor is disposed in the sample liquid accumulation portion.

* * * * *